(12) United States Patent
Allison

(10) Patent No.: US 9,737,434 B2
(45) Date of Patent: Aug. 22, 2017

(54) SYSTEMS AND METHODS WITH INTERRUPT/RESUME CAPABILITIES FOR TREATING SUBCUTANEOUS LIPID-RICH CELLS

(71) Applicant: Zeltiq Aesthetics, Inc., Pleasanton, CA (US)

(72) Inventor: John W. Allison, Los Altos, CA (US)

(73) Assignee: Zeltiq Aestehtics, Inc., Pleasanton, CA (US)

( * ) Notice: Subject to any disclaimer, the term of this patent is extended or adjusted under 35 U.S.C. 154(b) by 959 days.

(21) Appl. No.: 13/888,168

(22) Filed: May 6, 2013

(65) Prior Publication Data

US 2013/0245731 A1    Sep. 19, 2013

Related U.S. Application Data

(63) Continuation of application No. 12/337,544, filed on Dec. 17, 2008, now Pat. No. 8,603,073.

(51) Int. Cl.
*A61F 7/00* (2006.01)
*A61F 7/10* (2006.01)
*A61B 17/00* (2006.01)
*A61F 7/02* (2006.01)

(52) U.S. Cl.
CPC .............. *A61F 7/0085* (2013.01); *A61F 7/10* (2013.01); *A61B 2017/00106* (2013.01); *A61F 2007/0075* (2013.01); *A61F 2007/0095* (2013.01); *A61F 2007/029* (2013.01); *A61F 2007/0296* (2013.01)

(58) Field of Classification Search
CPC .. A61F 7/0085; A61F 7/10; A61F 2007/0075; A61F 2007/029; A61F 2018/00464; A61F 2018/00714; A61F 2018/00803
See application file for complete search history.

(56) References Cited

U.S. PATENT DOCUMENTS

| | | | |
|---|---|---|---|
| 681,806 A | 9/1901 | Mignault |
| 889,810 A | 6/1908 | Robinson |
| 2,516,491 A | 7/1950 | Swastek |
| 2,726,658 A | 12/1955 | Chessey |
| 2,766,619 A | 10/1956 | Tribus et al. |
| 2,851,602 A | 9/1958 | Cramwinckel et al. |
| 3,093,135 A | 6/1963 | Hirschhorn |

(Continued)

FOREIGN PATENT DOCUMENTS

| | | |
|---|---|---|
| AU | 2011253768 A1 | 6/2012 |
| CA | 2441489 A1 | 3/2005 |

(Continued)

OTHER PUBLICATIONS

Bohm et al., "Saline-enhanced radiofrequency ablation of breast tissue: an in vitro feasibility study," Invest Radiol, 2000, pp. 149-57, vol. 35—issue (3).

(Continued)

*Primary Examiner* — Kaitlyn Smith
(74) *Attorney, Agent, or Firm* — Perkins Coie LLP

(57) ABSTRACT

Systems for removing heat from a subject's subcutaneous lipid-rich regions, such as tissue, organs, cells, and so forth, are described herein. In various embodiments, the system includes a treatment device and a controller for controlling a treatment process. The controller is configured to detect and compensate for an interruption in the treatment process.

13 Claims, 8 Drawing Sheets

(56) References Cited

U.S. PATENT DOCUMENTS

| | | |
|---|---|---|
| 3,132,688 A | 5/1964 | Nowak |
| 3,133,539 A | 5/1964 | William et al. |
| 3,282,267 A | 11/1966 | Wiliam |
| 3,502,080 A | 3/1970 | Hirschhorn |
| 3,587,577 A | 6/1971 | Smirnov et al. |
| 3,591,645 A | 7/1971 | Selwitz |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Stumpf et al. |
| 3,942,519 A | 3/1976 | Shock |
| 3,948,269 A | 4/1976 | Zimmer |
| 3,986,385 A | 10/1976 | Johnston et al. |
| 3,993,053 A | 11/1976 | Grossan |
| 4,002,221 A | 1/1977 | Buchalter |
| 4,026,299 A | 5/1977 | Sauder |
| 4,140,130 A | 2/1979 | Storm, III |
| 4,149,529 A | 4/1979 | Copeland et al. |
| 4,178,429 A | 12/1979 | Scheffer |
| 4,202,336 A | 5/1980 | van Gerven et al. |
| 4,266,043 A | 5/1981 | Fujii et al. |
| 4,269,068 A | 5/1981 | Molina |
| 4,381,009 A | 4/1983 | Del Bon et al. |
| 4,396,011 A | 8/1983 | Mack et al. |
| 4,459,854 A | 7/1984 | Richardson et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt et al. |
| 4,741,338 A | 5/1988 | Miyamae et al. |
| 4,764,463 A | 8/1988 | Mason et al. |
| 4,802,475 A | 2/1989 | Weshahy et al. |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott |
| 5,007,433 A | 4/1991 | Hermsdorffer et al. |
| 5,018,521 A | 5/1991 | Campbell |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen et al. |
| 5,139,496 A | 8/1992 | Hed |
| 5,143,063 A | 9/1992 | Fellner |
| 5,148,804 A | 9/1992 | Hill et al. |
| 5,158,070 A | 10/1992 | Dory |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney |
| 5,327,886 A | 7/1994 | Chiu |
| 5,330,745 A | 7/1994 | McDow |
| 5,333,460 A | 8/1994 | Lewis et al. |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold |
| 5,351,677 A | 10/1994 | Kami et al. |
| 5,358,467 A | 10/1994 | Milstein et al. |
| 5,362,966 A | 11/1994 | Rosenthal et al. |
| 5,363,347 A | 11/1994 | Nguyen |
| 5,372,608 A | 12/1994 | Johnson |
| 5,386,837 A | 2/1995 | Sterzer |
| 5,411,541 A | 5/1995 | Bell et al. |
| 5,427,772 A | 6/1995 | Hagan |
| 5,433,717 A | 7/1995 | Rubinsky et al. |
| 5,456,703 A | 10/1995 | Beeuwkes, III |
| 5,472,416 A | 12/1995 | Blugerman et al. |
| 5,486,207 A | 1/1996 | Mahawili |
| 5,497,596 A | 3/1996 | Zatkulak |
| 5,501,655 A | 3/1996 | Rolt et al. |
| 5,505,726 A | 4/1996 | Meserol |
| 5,505,730 A | 4/1996 | Edwards |
| 5,507,790 A | 4/1996 | Weiss et al. |
| 5,514,105 A | 5/1996 | Goodman, Jr. et al. |
| 5,514,170 A | 5/1996 | Mauch |
| 5,516,505 A | 5/1996 | McDow |
| 5,531,742 A | 7/1996 | Barken |
| 5,562,604 A | 10/1996 | Yablon et al. |
| 5,571,801 A | 11/1996 | Segall et al. |
| 5,575,812 A | 11/1996 | Owens et al. |
| 5,603,221 A | 2/1997 | Maytal et al. |
| 5,628,769 A | 5/1997 | Saringer et al. |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay |
| 5,660,836 A | 8/1997 | Knowlton |
| 5,665,053 A | 9/1997 | Jacobs |
| 5,672,172 A | 9/1997 | Zupkas |
| 5,700,284 A | 12/1997 | Owens et al. |
| 5,725,483 A | 3/1998 | Podolsky |
| 5,733,280 A | 3/1998 | Avitall |
| 5,741,248 A | 4/1998 | Stern et al. |
| 5,746,736 A | 5/1998 | Tankovich |
| 5,755,663 A | 5/1998 | Larsen et al. |
| 5,755,753 A | 5/1998 | Knowlton |
| 5,755,755 A | 5/1998 | Panyard |
| 5,759,182 A | 6/1998 | Varney et al. |
| 5,759,764 A | 6/1998 | Polovina |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,814,040 A | 9/1998 | Nelson et al. |
| 5,817,050 A | 10/1998 | Klein |
| 5,817,149 A | 10/1998 | Owens et al. |
| 5,817,150 A | 10/1998 | Owens et al. |
| 5,830,208 A | 11/1998 | Muller |
| 5,833,685 A | 11/1998 | Tortal et al. |
| 5,844,013 A | 12/1998 | Kenndoff et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer et al. |
| 5,901,707 A | 5/1999 | Gon.cedilla.alves et al. |
| 5,902,256 A | 5/1999 | Benaron |
| 5,919,219 A | 7/1999 | Knowlton |
| 5,944,748 A | 8/1999 | Mager et al. |
| 5,948,011 A | 9/1999 | Knowlton |
| 5,954,680 A | 9/1999 | Augustine et al. |
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens et al. |

(56) References Cited

U.S. PATENT DOCUMENTS

| | | |
|---|---|---|
| 5,997,530 A | 12/1999 | Nelson et al. |
| 6,017,337 A | 1/2000 | Pira et al. |
| 6,023,932 A | 2/2000 | Johnston et al. |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | McClure et al. |
| 6,049,927 A | 4/2000 | Thomas et al. |
| 6,051,159 A | 4/2000 | Hao et al. |
| 6,071,239 A | 6/2000 | Cribbs et al. |
| 6,074,415 A | 6/2000 | Der Ovanesian |
| 6,093,230 A | 7/2000 | Johnson, III et al. |
| 6,102,885 A | 8/2000 | Bass |
| 6,104,952 A | 8/2000 | Tu et al. |
| 6,104,959 A | 8/2000 | Spertell et al. |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,150,148 A | 11/2000 | Nanda et al. |
| 6,152,952 A | 11/2000 | Owens et al. |
| 6,171,301 B1 | 1/2001 | Nelson et al. |
| 6,180,867 B1 | 1/2001 | Hedengren et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung et al. |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chomenky et al. |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee et al. |
| 7,054,685 B2 | 5/2006 | Dimmer et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |

(56) References Cited

U.S. PATENT DOCUMENTS

| | | |
|---|---|---|
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy et al. |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,397,518 B1 | 3/2013 | Vistakula et al. |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,764,693 B1 | 7/2014 | Graham et al. |
| 8,834,547 B2 | 9/2014 | Anderson et al. |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0156509 A1 | 10/2002 | Cheung |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0069618 A1 | 4/2003 | Smith et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0133251 A1 | 7/2004 | Altshuler et al. |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi et al. |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2005/0033957 A1 | 2/2005 | Enokida |
| 2005/0049526 A1 | 3/2005 | Baer |
| 2005/0049543 A1 | 3/2005 | Anderson et al. |
| 2005/0049661 A1 | 3/2005 | Koffroth |
| 2005/0113725 A1 | 5/2005 | Masuda |
| 2005/0143781 A1 | 6/2005 | Carbunaru et al. |
| 2005/0145372 A1 | 7/2005 | Noel |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0182462 A1 | 8/2005 | Chornenky et al. |
| 2005/0187495 A1 | 8/2005 | Quistgaard et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0261753 A1 | 11/2005 | Littrup et al. |
| 2005/0283144 A1 | 12/2005 | Shiono et al. |
| 2006/0030778 A1 | 2/2006 | Mendlein et al. |
| 2006/0035380 A1 | 2/2006 | Saint-Leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0122509 A1 | 6/2006 | Desilets |
| 2006/0189964 A1 | 8/2006 | Anderson et al. |

(56) References Cited

U.S. PATENT DOCUMENTS

| | | |
|---|---|---|
| 2006/0195168 A1 | 8/2006 | Dunbar et al. |
| 2006/0200063 A1 | 9/2006 | Munro et al. |
| 2006/0206040 A1 | 9/2006 | Greenberg et al. |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | DeLonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0073367 A1 | 3/2007 | Jones et al. |
| 2007/0078502 A1 | 4/2007 | Weber et al. |
| 2007/0100398 A1 | 5/2007 | Sloan |
| 2007/0106342 A1 | 5/2007 | Schumann |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1 | 8/2007 | Anderson |
| 2007/0198071 A1 | 8/2007 | Ting et al. |
| 2007/0219540 A1 | 9/2007 | Masotti et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1 | 11/2007 | Levinson et al. |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0183164 A1 | 7/2008 | Elkins et al. |
| 2008/0188915 A1 | 8/2008 | Mills et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0312651 A1 | 12/2008 | Pope et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0221938 A1 | 9/2009 | Rosenberg et al. |
| 2009/0276018 A1 | 11/2009 | Brader |
| 2009/0281464 A1 | 11/2009 | Cioanta et al. |
| 2009/0306749 A1 | 12/2009 | Mulindwa |
| 2009/0312676 A1 | 12/2009 | Rousso et al. |
| 2009/0312693 A1 | 12/2009 | Thapliyal et al. |
| 2009/0326621 A1 | 12/2009 | El-Galley |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |
| 2010/0179531 A1 | 7/2010 | Nebrigic et al. |
| 2010/0198064 A1 | 8/2010 | Perl et al. |
| 2010/0217349 A1 | 8/2010 | Fahey et al. |
| 2010/0268220 A1 | 10/2010 | Johnson et al. |
| 2010/0280582 A1 | 11/2010 | Baker et al. |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Kreindel |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic et al. |
| 2011/0238050 A1 | 9/2011 | Allison et al. |
| 2011/0238051 A1 | 9/2011 | Levinson et al. |
| 2011/0257642 A1 | 10/2011 | Griggs, III |
| 2011/0300079 A1 | 12/2011 | Martens et al. |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams, III et al. |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark, III et al. |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158636 A1 | 6/2013 | Ting et al. |
| 2013/0166003 A1 | 6/2013 | Johnson et al. |
| 2013/0185440 A1 | 7/2013 | Blau et al. |
| 2013/0190744 A1 | 7/2013 | Avram et al. |
| 2013/0238062 A1 | 9/2013 | Ron Edoute et al. |
| 2013/0245507 A1 | 9/2013 | Khorassani Zadeh |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0303904 A1 | 11/2013 | Barthe et al. |
| 2013/0303905 A1 | 11/2013 | Barthe et al. |
| 2013/0331914 A1 | 12/2013 | Lee et al. |

(56) References Cited

U.S. PATENT DOCUMENTS

| | | |
|---|---|---|
| 2014/0005759 A1 | 1/2014 | Fahey et al. |
| 2014/0005760 A1 | 1/2014 | Levinson et al. |
| 2014/0142469 A1 | 5/2014 | Britva et al. |
| 2014/0200487 A1 | 7/2014 | Ramdas et al. |
| 2014/0200488 A1 | 7/2014 | Seo et al. |
| 2014/0222121 A1 | 8/2014 | Spence et al. |
| 2014/0277219 A1 | 9/2014 | Nanda |
| 2014/0277302 A1 | 9/2014 | Weber et al. |
| 2014/0303697 A1 | 10/2014 | Anderson et al. |
| 2015/0209174 A1 | 7/2015 | Abreu |
| 2015/0216719 A1 | 8/2015 | DeBenedictis et al. |
| 2015/0216720 A1 | 8/2015 | DeBenedictis et al. |
| 2015/0216816 A1 | 8/2015 | O'Neil et al. |
| 2015/0223975 A1 | 8/2015 | Anderson et al. |
| 2015/0328077 A1 | 11/2015 | Levinson |
| 2015/0335468 A1 | 11/2015 | Rose et al. |
| 2015/0342780 A1 | 12/2015 | Levinson et al. |
| 2016/0051308 A1 | 2/2016 | Pennybacker et al. |
| 2016/0051401 A1 | 2/2016 | Yee et al. |
| 2016/0135985 A1 | 5/2016 | Anderson |
| 2016/0324684 A1 | 11/2016 | Levinson et al. |

FOREIGN PATENT DOCUMENTS

| | | |
|---|---|---|
| CA | 2585214 A1 | 10/2007 |
| CH | 333982 A | 11/1958 |
| CN | 86200604 U | 10/1987 |
| CN | 2514795 Y | 10/2002 |
| CN | 2514811 Y | 10/2002 |
| CN | 1511503 | 7/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| CN | 101259329 A | 9/2008 |
| CN | 101309657 A | 11/2008 |
| DE | 532976 C | 9/1931 |
| DE | 2851602 | 6/1980 |
| DE | 4213584 A1 | 11/1992 |
| DE | 4224595 | 1/1994 |
| DE | 4238291 A1 | 5/1994 |
| DE | 4445627 A1 | 6/1996 |
| DE | 19800416 A1 | 7/1999 |
| EP | 0263069 A2 | 4/1988 |
| EP | 0397043 | 11/1990 |
| EP | 0406244 A1 | 1/1991 |
| EP | 0598824 A1 | 6/1994 |
| EP | 1030611 A1 | 8/2000 |
| EP | 1201266 A1 | 5/2002 |
| EP | 1568395 A1 | 8/2005 |
| EP | 2260801 A2 | 12/2010 |
| EP | 2289598 A1 | 3/2011 |
| EP | 2527005 A1 | 11/2012 |
| FR | 854937 A | 4/1940 |
| FR | 2744358 A1 | 8/1997 |
| FR | 2745935 A1 | 9/1997 |
| FR | 2767476 A1 | 2/1999 |
| FR | 2776920 A1 | 10/1999 |
| FR | 2789893 A1 | 8/2000 |
| FR | 2805989 A1 | 9/2001 |
| GB | 387960 A | 2/1933 |
| GB | 2120944 A | 12/1983 |
| GB | 2248183 A | 4/1992 |
| GB | 2263872 A | 8/1993 |
| GB | 2286660 A | 8/1995 |
| GB | 2323659 A | 9/1998 |
| JP | 58187454 | 11/1983 |
| JP | 63076895 A | 4/1988 |
| JP | S6382936 A | 4/1988 |
| JP | 01223961 A | 9/1989 |
| JP | 03051964 A | 3/1991 |
| JP | 3259975 A | 11/1991 |
| JP | 4093597 A | 3/1992 |
| JP | H06261933 A | 9/1994 |
| JP | 6282977 A | 10/1994 |
| JP | 7194666 | 8/1995 |
| JP | 7268274 A | 10/1995 |
| JP | 09164163 A | 6/1997 |
| JP | 10216169 A | 8/1998 |
| JP | 10223961 A | 8/1998 |
| JP | 2000503154 A | 3/2000 |
| JP | 3065657 B2 | 7/2000 |
| JP | 2001046416 A | 2/2001 |
| JP | 2002125993 A | 5/2002 |
| JP | 2002224051 A | 8/2002 |
| JP | 2002282295 A | 10/2002 |
| JP | 2002290397 A | 10/2002 |
| JP | 2002543668 A | 12/2002 |
| JP | 2003190201 A | 7/2003 |
| JP | 2004013600 A | 1/2004 |
| JP | 2004073812 A | 3/2004 |
| JP | 2004159666 A | 6/2004 |
| JP | 2005039790 A | 2/2005 |
| JP | 3655820 | 3/2005 |
| JP | 200565984 | 3/2005 |
| JP | 2005110755 A | 4/2005 |
| JP | 2005509977 A | 4/2005 |
| JP | 2005520608 | 7/2005 |
| JP | 2005237908 A | 9/2005 |
| JP | 2005323716 A | 11/2005 |
| JP | 2006026001 A | 2/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |
| JP | 2009189757 A | 8/2009 |
| KR | 200173222 Y1 | 12/1999 |
| KR | 102004009450 | 11/2004 |
| KR | 20090000258 U | 1/2009 |
| KR | 1020130043299 A | 4/2013 |
| KR | 1020140038165 A | 3/2014 |
| RU | 2036667 01 | 6/1995 |
| SU | 532976 A1 | 11/1978 |
| TW | 0476644 | 2/2002 |
| WO | WO-8503216 A1 | 8/1985 |
| WO | 9114417 A1 | 10/1991 |
| WO | WO-9404116 A1 | 3/1994 |
| WO | 9623447 A1 | 8/1996 |
| WO | 9626693 A1 | 9/1996 |
| WO | WO-96/36293 | 11/1996 |
| WO | WO-96/37158 | 11/1996 |
| WO | 9704832 A1 | 2/1997 |
| WO | WO-97/05828 | 2/1997 |
| WO | WO-9722262 A2 | 6/1997 |
| WO | 9724088 A1 | 7/1997 |
| WO | WO-9725798 A1 | 7/1997 |
| WO | 9748440 A1 | 12/1997 |
| WO | 9829134 A2 | 7/1998 |
| WO | 9831321 A1 | 7/1998 |
| WO | WO-98/41157 | 9/1998 |
| WO | WO-9841156 A1 | 9/1998 |
| WO | 9909928 A1 | 3/1999 |
| WO | 9916502 A1 | 4/1999 |
| WO | WO-9938469 A1 | 8/1999 |
| WO | 9949937 A1 | 10/1999 |
| WO | WO-00/44346 | 8/2000 |
| WO | WO-0044349 A1 | 8/2000 |
| WO | WO-00/65770 A1 | 11/2000 |
| WO | WO-0067685 A1 | 11/2000 |
| WO | 0100269 A1 | 1/2001 |
| WO | 0113989 A1 | 3/2001 |
| WO | WO-0114012 A1 | 3/2001 |
| WO | 0134048 A1 | 5/2001 |
| WO | WO-0205736 A2 | 1/2002 |
| WO | WO-02/102921 | 12/2002 |
| WO | WO-03007859 A1 | 1/2003 |
| WO | WO-03078596 A2 | 9/2003 |
| WO | 03079916 A1 | 10/2003 |
| WO | WO-2004/000098 | 12/2003 |
| WO | WO-2004080279 A2 | 9/2004 |
| WO | WO-2004090939 A2 | 10/2004 |

(56) References Cited

FOREIGN PATENT DOCUMENTS

| WO | WO-2005033957 A1 | 4/2005 |
|---|---|---|
| WO | WO-2005046540 A1 | 5/2005 |
| WO | 2005060354 A2 | 7/2005 |
| WO | WO-2005096979 A1 | 10/2005 |
| WO | 2005112815 A1 | 12/2005 |
| WO | WO-2006/066226 | 6/2006 |
| WO | WO-2006094348 A1 | 9/2006 |
| WO | WO-2006106836 A1 | 10/2006 |
| WO | 2006116603 A2 | 11/2006 |
| WO | WO-2006127467 A2 | 11/2006 |
| WO | WO-2007012083 A2 | 1/2007 |
| WO | 2007028975 A1 | 3/2007 |
| WO | WO-2007041642 A2 | 4/2007 |
| WO | WO-2007101039 A1 | 9/2007 |
| WO | WO-2007127924 A2 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | WO-2008039557 A1 | 4/2008 |
| WO | 2008055243 A2 | 5/2008 |
| WO | WO-2008143678 A1 | 11/2008 |
| WO | WO-2009/011708 A1 | 1/2009 |
| WO | WO-2009026471 A1 | 2/2009 |
| WO | WO-2010077841 A1 | 7/2010 |
| WO | WO-2010127315 A2 | 11/2010 |
| WO | WO-2012012296 A1 | 1/2012 |
| WO | WO-2012103242 A1 | 8/2012 |
| WO | 2013013059 A1 | 1/2013 |
| WO | 2013075006 A1 | 5/2013 |
| WO | 2013075016 A1 | 5/2013 |
| WO | 2013190337 A1 | 12/2013 |

OTHER PUBLICATIONS

European Search Report, European Application No. EP07758558.6; Applicant: Zeltiq Aesthetics, Inc.; dated Jul. 20, 2007, 4 pages.
European Search Report, European Patent Application No. 10167756.5, Applicant: The General Hospital Corporation, dated Aug. 31, 2010, 6 pages.
European Search Report, Eurpean Patent Application No. EP07761461; Applicant: Zeltiq Aesthetics, Inc., dated Apr. 25, 2012, 9 pages.
European Search Report, Supplement, European Patent Application No. EP08798416.7, Applicant: Zeltiq Aesthetics, Inc., dated Jan. 12, 2012, 7 pages.
European Search Report, Supplement, European Patent Application No. EP09836823, Applicant: Zeltiq Aesthetics, Inc., dated May 15, 2012, 5 pages.
Final Office Action; U.S. Appl. No. 11/435,502; dated Mar. 29, 2010, 11 pages.
Final Office Action; U.S. Appl. No. 11/528,225; dated Dec. 29, 2010, 9 pages.
Final Office Action; U.S. Appl. No. 11/558,046; dated Mar. 30, 2011, 17 pages.
Final Office Action; U.S. Appl. No. 11/741,271; dated Jul. 19, 2012, 8 pages.
Final Office Action; U.S. Appl. No. 11/750,953; dated Jul. 5, 2012, 11 pages.
Hale et al., "Influence of chronic heat exposure and prolonged food deprivation on execretion of magnesium, phosphorus, calcium, hydrogen ion & ketones," Aerosp Med, 1968, pp. 919-26, vol. 39—issue (9).
International Search Report and Written Opinion for PCT/US2005/045988; Applicant: The General Hospital Corporation; dated Apr. 25, 2006, 14 pages.
International Search Report and Written Opinion for PCT/US2007/062508; Applicant: Juniper Medical, Inc.; dated Jul. 20, 2007, 13 pages.
International Search Report and Written Opinion for PCT/US2009/067973; Applicant: Zeltiq Aesthetics, Inc.; dated Feb. 18, 2010, 10 pages.
International Search Report and Written Opinion for PCT/US2010/033290; Applicant: Zeltiq Aesthetics, Inc.; dated Feb. 25, 2011, 12 pages.
International Search Report and Written Opinion for PCT/US2011/022112; Applicant: Zeltiq Aesthetics, Inc.; dated Mar. 18, 2011, 11 pages.
International Search Report and Written Opinion for PCT/US2011/022444; Applicant: Zeltiq Aesthetics, Inc., dated Mar. 29, 2011, 14 pages.
International Search Report and Written Opinion for PCT/US2012/022585; dated May 18, 2012, 14 pages.
Koska, J. et al., "Endocrine Regulation of Subcutaneous Fat Metabolism During Cold Exposure in Humans," Ann N.Y. Acad, Sci., 967:500-05, 2002.
Kundu et al., "Breath acetone analyzer: diagnostic tool to monitor dietary fat loss," Clin Chem, 1993, pp. 87-92, vol. 39, issue (1).
Laugier, et al., "In Vivo Results with a New Device for Ultrasonic Monitoring of Pig Skin Cryosurgery: The Echographic Cryoprobe," The society for Investigative Dermatology, Inc., vol. 111(2), Aug. 1998.
Lidagoster, MD et al., "Comparison of Autologous Fat Transfer in Fresh, Refrigerated, and Frozen Specimens: An Animal Model Presented," at the 16th Annual Meeting of the Northeastern Society of Plastic Surgeons: Burlington, VT, 1999, pp. 512-515.
Merrill, Tom, "A Chill to the Heart: A System to Deliver Local Hypothermia Could One Day Improve the Lives of Heart-Attack Patients," Mechanical Engineering Magazine, Oct. 2010 (10 pages).
Murphy, J.V. et al., "Frostbite: Pathogenesis and Treatment," The Journal of Trauma: Injury, Infection, and Critical Care, 48(1):171-178, 2000.
Non-Final Office Action; U.S. Appl. No. 10/391,221; dated Jan. 25, 2006, 6 pages.
Non-Final Office Action; U.S. Appl. No. 10/391,221; dated May 30, 2007, 8 pages.
Non-Final Office Action; U.S. Appl. No. 10/391,221; dated Jul. 22, 2005, 6 pages.
Non-Final Office Action; U.S. Appl. No. 11/528,189; dated Apr. 6, 2012, 9 pages.
Non-Final Office Action; U.S. Appl. No. 11/528,225; dated Apr. 12, 2010, 11 pages.
Non-Final Office Action; U.S. Appl. No. 11/528,225; dated Aug. 3, 2011, 11 pages.
Non-Final Office Action; U.S. Appl. No. 11/558,046; dated Jul. 12, 2010, 14 pages.
Non-Final Office Action; U.S. Appl. No. 11/741,271; dated Jul. 12, 2010, 9 pages.
Non-Final Office Action; U.S. Appl. No. 11/777,992; dated Jun. 22, 2012, 5 pages.
Non-Final Office Action; U.S. Appl. No. 12/565,613; dated Sep. 23, 2011, 32 pages.
Non-Final Office Action; U.S. Appl. No. 12/942,852; dated Mar. 7, 2011, 6 pages.
Non-Final Office Action; U.S. Appl. No. 12/942,852; dated Jun. 30, 2011, 10 pages.
Pre-Interview Office Action; U.S. Appl. No. 11/434,478; dated May 6, 2010, 4 pages.
Rabi, "Metabolic adaptations in brown adipose tissue of the hamster in extreme ambient temperatures," American Journal of Physiology 231, 153-160 (1976).
Renold, A.E., "Adipose Tissue," Handbook of Physiology, Chapter 15:170-76, 1965.
Rubinsky, "Cryosurgery: advances in the application of low temperatures to medicine," Int. J. Refrig. 190-199 (1991).
Wang et al., "Cryopreservation of cell/hydrogel constructs based on a new cell-assembling technique", Sep. 5, 2009, 40 pages.
Ardevol, "Cooling rates of tissue samples during freezing with liquid nitrogen," J. of Biochem and Biophysical Methods, 27, 77-86 (1993).
Bondei, E. et al., "Disorders of Subcutaneous Tissue (Cold Panniculitis)," Dermatology in General Medicine, Chapter 108, Section 16: 1333-1334, 1993.

(56) References Cited

OTHER PUBLICATIONS

Burge, S.M. et al., "Hair Follicle Destruction and Regeneration in Guinea Pig Skin after Cutaneous Freeze Injury," Cryobiology, 27(2): 153-163, 1990.
Coban, "Ischemia-Reperfusion Injury of Adipofascial Tissue: An Experimental Study Evaluating early Histologic and Biochemical Alterations in Rats," Mediators of Inflammation, 2005, 5, 304-308.
Donski et al., "The Effects of Cooling no Experimental Free Flap Survival," Brit J Plas Surg, 1980, pp. 353-360, vol. 33.
Duncan, W.C. et al., "Cold Panniculitis," Arch. Derm., 94:722-24, 1966.
Epstein, E.H. et al., "Popsicle Panniculitis," The New England Journal of Medicine, 282(17):996-67, 1970.
Final Office Action; U.S. Appl. No. 10/391,221; dated Aug. 24, 2006, 4 pages.
Final Office Action; U.S. Appl. No. 11/016,196; dated Mar. 23, 2010, 12 pages.
Gage, "Current Progress in Cryosurgery," Cryobiology 25, 483-486 (1988).
Heller-Page et al., "Temperature-dependent skin disorders," Journal of the American Academy of Dermatology, May 1988, vol. 18, No. 5, Pt 1, pp. 1003-1019.
Hemmingsson, "Attenuation in Human muscle and Fat Tissue in Vivo and in Vitro," Acta Radiologica Diagnosis 23, 149-151 (1982).
Henry et al.,"Les Dermatoses Hivernales," Rev Med Liege, 1999, 54:11, 864-866. [Abstract Attached].
Holman, "Variation in cryolesion penetration due to probe size and tissue thermal conductivity," Ann. Thorac. Surg. 53, 123-126 (1992).
Hong, "Patterns of Ice Formulation in Normal and Malignant Breast Tissue," Cryobiology 31, 109-120 (1994).
International Search Report and Written Opinion for PCT/US2007/023492; Applicant: Zeltiq Aesthetics, Inc.; dated May 15, 2008, 7 pages.
International Search Report and Written Opinion for PCT/US2007/064016; Applicant: Juniper Medical, Inc.; dated Jul. 20, 2007, 13 pages.
International Search Report and Written Opinion for PCT/US2007/064017; Applicant: Juniper Medical, Inc.; dated Oct. 26, 2007, 16 pages.
International Search Report and Written Opinion for PCT/US2007/064018; Applicant: Juniper Medical, Inc.; dated Jul. 26, 2007, 13 pages.
International Search Report and Written Opinion for PCT/US2007/067638; Applicant: Juniper Medical, Inc.; dated Jan. 10, 2008, 11 pages.
International Search Report and Written Opinion for PCT/US2007/069694; Applicant: Juniper Medical, Inc.; dated Nov. 23, 2007, 12 pages.
International Search Report and Written Opinion for PCT/US2007/075935; Applicant: Zeltiq Aesthetics, Inc.; dated Apr. 10, 2008, 12 pages.
International Search Report and Written Opinion for PCT/US2007/083255; Applicant: Zeltiq Aesthetics, Inc.; dated Aug. 11, 2008, 8 pages.
International Search Report and Written Opinion for PCT/US2008/073930; Applicant: Zeltiq Aesthetics, Inc.; dated Nov. 7, 2008, 10 pages.
International Search Report and Written Opinion for PCT/US2009/058088; Applicant: Zeltiq Aesthetics, Inc.; dated Nov. 20, 2009, 14 pages.
Kellum, R.E. et al., "Sclerema Neonatorum: Report of Case and Analysis of Subcutaneous and Epidermal-Dermal Lipids by Chromatographic Methods," Arch. Derm., 97:372-80, 1968.
Kundu et al., "Novel solid-phase assay of ketone bodies in urine," Clin Chem, 1991, pp. 1565-1569, vol. 37—issue (9).
Kuroda et al., "Thermal distribution of radio-frequency inductive hyperthermia using an inductive aperture-type applicator: evaluation of the effect of tumour size and depth," Med Biol Eng Comput, 1999, pp. 285-290, vol. 37—issue (3).

Levchenko, et al., "Effect of dehydration on lipid metabolism," WMJ, 1978, pp. 95-97, vol. 50—issue (1).
Liu, A.Y.C. et al., "Transient Cold Shock Induces the Heat Shock Response upon Recovery at 37 C in Human Cells," J. Biol. Chem., May 20, 1994, 269(20), 14768-14775.
Lvova, "Lipid levels and lipid peroxidation in frog tissues during hypothermia and hibernation," WMJ, 1990, pp. 65-70, vol. 62—issue (1).
Maize, J.C., "Panniculitis," Cutaneous Pathology, Chapter 13:327-344, 1998.
Malcolm, G. et al., "Fatty Acid Composition of Adipose Tissue in Humans: Differences between Subcutaneous Sites," Am J Clin. Nutr., 50(2):288-91, 1989.
Moschella, S.L. et al., "Diseases of the Subcutaneous Tissue," Derm., Section 2:1169-1181, 1985.
Nagao et al., "Dietary diacylglycerol suppresses accumulation of body fat compared to triacylglycerol in men a double-blind controlled trial," J Nutr, 2000, pp. 792-797, vol. 130—issue (4).
Nagore et al., "Lipoatrophia semicircularis-a traumatic panniculitis: Report of seven cases and review of the literature," Journal of the American Academy of Dermatology, Nov. 1998, 39:879-81.
Nielsen, "Thermoregulation in Rest and Exercise," Acta Phys Scan Supp, 1969, pp. 6-74, vol. 323.
Nishikawa, "Ultrastructural Changes and Lipid Peroxidation in Rat Adipomusculocutaneous Flap Isotransplants after Normothermic Storage and Reperfusion," Transplantation, 1992, 54, 795-801.
Non-Final Office Action; U.S. Appl. No. 11/016,196; dated Apr. 22, 2008, 11 pages.
Non-Final Office Action; U.S. Appl. No. 11/016,196; dated Sep. 25, 2009, 8 pages.
Non-Final Office Action; U.S. Appl. No. 11/359,092; dated Nov. 19, 2009, 13 pages.
Non-Final Office Action; U.S. Appl. No. 11/435,502; dated Jul. 17, 2009, 10 pages.
Pease, "An Integrated Probe for Magnetic Resonance Imaging Monitored Skin Cryosurgery," Journal of Biomedical Engineering 117, 59-63, (1995).
Pech, "Attenuation values, volume changes and artifacts in tissue due to freezing," Acta Radiologica 6, 779-782 (1987).
Peterson et al., "Bilateral Fat Necrosis of the Scrotum, Urology Service, Department of Surgery, Dermatology Service, Department of Medicine and Department of Pediatrics," Letterman Army Medical Center, Journal of Urology, 1976, pp. 825-826, vol. 116, The Williams & Wilkins Co.
Phinney, S.D. et al., "Human Subcutaneous Adipose Tissue Shows Site-Specific Differences in Fatty Acid Composition," Am J. Clin. Nutr., 60:725-29, 1994.
Schoning, et al., "Experimental Frostbite: Freezing Times, Rewarming Times, and Lowest Temperatures of Pig Skin Exposed to Chilled Air," Cryobiology, 1990, pp. 189-193, 27.
Shephard, "Adaptation to Exercise in the Cold," Sports Medicine, 1985, 2:59-71.
Wharton et al., "Cold acclimation and cryoprotectants in a freeze-tolerant Antarctic nematode, *Panagrolaimus davidi*," Mar. 7, 2000, 2 pages.
Winkler et al., "Gene Transfer in Laboratory Fish: Model Organisms for the Analysis of Gene Function," Transgenic Animals, 1997, pp. 387-395.
Young, H.E. et al., "Isolation of Embryonic Chick Myosatellite and Pluripotent Stem Cells, " J. Tiss. Cult. Meth., 14:85-92, 1992.
International Preliminary Examining Authority Written Opinion for PCT/US2007/67638; Application Levinson et al. dated Jun. 8, 2010.
International Preliminary Examining Authority Written Opinion for PCT/US2007/67638; Application Levinson et al. dated Sep. 21, 2010, 7 pages.
International Search Report and Written Opinion for PCT/US2011/044270; Applicant: Zeltiq Aesthetics, Inc.; dated Nov. 21, 2011. 9 pages.
Non-Final Office Action; U.S. Appl. No. 12/337,544; dated Mar. 30, 2012, 13 pgs.
Pierard, G.E., Nizet, J.L., Pierard-Franchimont, C., "Cellulite: From Standing Fat Herniation to Hypodermal Stretch Marks," Am. J. Dermatol. 22:1, 34-37, 2000.

(56) References Cited

OTHER PUBLICATIONS

Pope, "Selective Firbous Septae Heating", Thermage Article, Feb. 2005, 7pgs.
Quinn, P.J., "A Lipid Phase Separation Model of Low Temperature Damage to Biological Membranes" Cryobiology, 22: 128-147, 1985.
Sigma-Aldrich "Polyethylene glycol and Polyethylene oxide," http://www.sigmaaldrich.com/materials-science/materialscience-;products.htmi?TablePage=2020411 0, accessed Oct. 19, 2012.
European Search Report; Application No. EP10770461; dated Aug. 31, 2012; Applicant: Zeltiq Aesthetics, Inc. 5 pgs.
Non-Final Office Action; U.S. Appl. No. 12/840,235; dated Apr. 11, 2013; 9 pages.
Manstein et al. "A Novel Cryotherapy Method of Non-invasive, Selective Lipolysis" LasersSurg.Med 40:S20 p. 104 (2008).
Manstein et al."Selective Cryolysis: A Novel Method of Non-Invasive Fat Removal", LasersSurg.Med. 40:595-604 (2008).
Nagle W.A., Soloff, B.L., Moss, A.J. Jr., Henle K.J. "Cultured Chinese Hamster Cells Undergo Apoptosis After Exposure to Cold but Nonfreezing Temperatures" Cryobiology 27, 439-451 (1990).
Narins, "Non-Surgical Radiofrequency Facelift", 2003, 495-500, 6 pgs.
Mazur, P. "Cryobiology: the Freezing of Biological Systems" Science, 68: 939-949 (1970).
Rubinsky, B., "Principles of Low Temperature Preservation" Heart Failure Reviews, 8, 277-284 (2003).
Thermage, News Release, "Study Published in Facial Plastic Surgery Journal Finds Selective Heating of Fibrous Septae Key to Success and Safety of Thermage ThermoCool System", Jun. 20, 2005, 2 pages.
Vallerand, A.L., Zamecnik. J., Jones, P.J.H. Jacobs, I. "Cold Stress Increases Lipolysis, FFA RA and TG/FFA Cycling in Humans" Aviation, Space, and Environmental Medicine 70, 42-50 (1999).
Rossi, "Cellulite: a Review" 2000, 251-262, 12 pgs.
"ThermaCool Monopolar Capacitive Radiofrequency",The one choice for nonabliative tissue tightening and contouring, Tech Brochure, Nov. 30, 2005, 8 pgs.
"So-Called Cellulite: An Invetnted Disease", Nurnberger, Journal Title: Journal of dermatologic surgery and oncology, Mar. 1978, 14 pgs.
"Effect of Controlled Volumetric Tissue Heating with Radiorequency on Cellulite and the Subcutaneous Tissue of the Bottocks and Thighs". Del Pino, 2006, 9 pgs.
Mayoral, "Skin Tightening with a Combined Unipolar and Bipolar Radiofrequency Device" , 2007 Journal of Drugs in Dermatology, 4 pgs.
Becker, "Local Temperature Rises Influence In Vivo Electroporation Pore Development: A Numerical Stratum Corneum Lipid Phase Transition Model", Oct. 2007, 10 pgs.
Miklavcic, "Electroporation-Based Technologies and Treatments", 2010 236:1-2, 2 pgs.
Nanda, "Studies on electroporation of thermally and chemically treated human erythocytes", May 28, 1993 in revised form Mar. 7, 1994, 6 pgs.
BioMedical Engineering OnLine, "High-Frequency Irreversible electroporation (H-FIRE) for non-thermal ablation without muscle contraction", Nov. 21, 2011, 21 pgs.
Al-Sakere, "Tumor Ablation with Irreversible Electroporation", Nov. 2007, Issue 11, 8 pgs.
Non-Final Office Action, U.S. Appl. No. 13/616,497, dated Jun. 28, 2013, 38 pages.
PubMed, "Effects of thermal shocks on interleukin-1 levels and heat shock protein 72 (HSP72) expression in normal human keratinocytes", Arch Dermatol Res. 1992; 284(7): 414-7.
PubMed, "Cold shock induces the synthesis of stress proteins in human kerantinocytes", Holland DB. Aug. 1993; 101(2): 196-9.
Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.
Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.
Ardevol et al., "Cooling Rates of Tissue Samples During Freezing with Liquid Nitrogen," Journal of Biochemical and Biophysical Methods, 27, 1993, pp. 77-86.
Duck, F. A., Physical Properties of Tissue, Academic Press Ltd., chapters 4 & 5, 1990, pp. 73-165.
Fournier, L. et al. "Lattice Model for the Kinetics of Rupture of Fluid Bilayer Membranes," Physical Review, vol. 67, 2003, pp. 051908-1-051908-11.
Gabriel, S. et al., "The Dielectric Properties of Biological Tissues: II. Measurements in the Frequency Range 10 Hz to 20 GHz," Physics in Medicine and Biology, vol. 41, 1996, pp. 2251-2269.
Isambert, H. "Understanding the Electroporation of Cells and Artificial Bilayer Membranes," Physical Review Letters, vol. 80, No. 15, 1998, pp. 3404-3707.
Peterson, L. J. et al., "Bilateral Fat Necrosis of the Scrotum," Journal of Urology, vol. 116, 1976, pp. 825-826.
Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.
Schoning, P. et al., "Experimental Frostbite: Freezing Times, Rewarming Times, and Lowest Temperatures of Pig Skin Exposed to Chilled Air," Cryobiology 27, 1990, pp. 189-193.
Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.
Hernan, P. et al., "Study for the evaluation of the efficacy of Lipocryolysis (EEEL)", Nov. 30, 2011.
Hernan, R. P., "A Study to Evaluate the Action of Lipocryolysis", 33(3) CryoLellers, 2012, pp. 176-180.
Jalian, H. R. et al., "Cryolipolysis: A Historical Perspective and Current Clinical Practice", 32(1) Semin. Cutan. Med. Surg., 2013, pp. 31-34.
Zelickson, B. et al., "Cryolipolysis for Noninvasive Fat Cell Destruction: Initial Results from a Pig Model", 35 Dermatol. Sug., 2009, pp. 1-9.

SYSTEMS AND METHODS WITH INTERRUPT/RESUME CAPABILITIES FOR TREATING SUBCUTANEOUS LIPID-RICH CELLS

CROSS REFERENCE TO RELATED APPLICATION

The present application is a continuation of U.S. patent application Ser. No. 12/337,544, filed Dec. 17, 2008, now U.S. Pat. No. 8,603,073, the disclosure of which is incorporated herein by reference in its entirety.

TECHNICAL FIELD

The present application relates generally to treatment systems and methods with interrupt/resume capabilities for cooling subcutaneous lipid-rich cells.

BACKGROUND

Excess body fat, or adipose tissue, may be present in various locations of the body, including, for example, the thigh, buttocks, abdomen, knees, back, face, arms, chin, and other areas. Moreover, excess adipose tissue is thought to magnify the unattractive appearance of cellulite, which forms when subcutaneous fat protrudes into the dermis and creates dimples where the skin is attached to underlying structural fibrous strands. Cellulite and excessive amounts of adipose tissue are often considered to be unappealing. Moreover, significant health risks may be associated with higher amounts of excess body fat.

A variety of methods have been used to treat individuals having excess body fat and, in many instances, non-invasive removal of excess subcutaneous adipose tissue can eliminate unnecessary recovery time and discomfort associated with invasive procedures such as liposuction. Conventional non-invasive treatments for removing excess body fat typically include topical agents, weight-loss drugs, regular exercise, dieting, or a combination of these treatments. One drawback of these treatments is that they may not be effective or even possible under certain circumstances. For example, when a person is physically injured or ill, regular exercise may not be an option. Similarly, weight-loss drugs or topical agents are not an option when they cause an allergic or negative reaction. Furthermore, fat loss in selective areas of a person's body often cannot be achieved using general or systemic weight-loss methods.

Other methods designed to reduce subcutaneous adipose tissue include laser-assisted liposuction and mesotherapy. Newer non-invasive methods include applying radiant energy to subcutaneous lipid-rich cells via, e.g., radio frequency and/or light energy, such as described in U.S. Patent Publication No. 2006/0036300 and U.S. Pat. No. 5,143,063, or via, e.g., high intensity focused ultrasound (HIFU) radiation such as described in U.S. Pat. Nos. 7,258,674 and 7,347,855. Additional methods and devices for non-invasively reducing subcutaneous adipose tissue by cooling are disclosed in, e.g., Manstein et al. "A Novel Cryotherapy Method of Non-invasive, Selective Lipolysis" LasersSurg. Med. 40:S20 p 104 (2008), Manstein et al., "Selective Cryolysis: A Novel Method of Non-Invasive Fat Removal", LasersSurg. Med. 40:595-604 (2008), U.S. Pat. No. 7,367,341 entitled "METHODS AND DEVICES FOR SELECTIVE DISRUPTION OF FATTY TISSUE BY CONTROLLED COOLING" to Anderson et al.; U.S. Patent Publication No. 2005/0251120 entitled "METHODS AND DEVICES FOR DETECTION AND CONTROL OF SELECTIVE DISRUPTION OF FATTY TISSUE BY CONTROLLED COOLING" to Anderson et al.; U.S. Patent Publication No. 2007/0198071 entitled "COOLING DEVICE FOR REMOVING HEAT FROM SUBCUTANEOUS LIPID-RICH CELLS" to Ting et al.; U.S. Patent Publication No. 2007/0255362 entitled "CRYOPROTECTANT FOR USE WITH A TREATMENT DEVICE FOR IMPROVED COOLING FOR SUBCUTANEOUS LIPID-RICH CELLS" to Levinson et al.; U.S. Patent Publication No. 2008/0077201 entitled "COOLING DEVICE WITH FLEXIBLE SENSORS" to Levinson et al.; U.S. Patent Publication No. 2008/0077211 entitled "COOLING DEVICE HAVING A PLURALITY OF CONTROLLABLE COOLING ELEMENTS TO PROVIDE A PREDETERMINED COOLING PROFILE" to Levinson et al.; U.S. Patent Publication No. 2008/0287839 entitled "METHOD OF ENHANCED REMOVAL OF HEAT FROM SUBCUTANEOUS LIPID-RICH CELLS AND TREATMENT APPARATUS HAVING AN ACTUATOR" to Rosen et al., filed May 18, 2007; U.S. patent application Ser. No. 11/777,992 entitled "SYSTEM FOR TREATING LIPID-RICH REGIONS" to Levinson et al., filed Jul. 13, 2007, the entire disclosures of which are incorporated herein by reference. Although the methods and devices disclosed in these publications and applications are promising, several improvements for enhancing the implementation of these methods and devices would be desirable.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

DETAILED DESCRIPTION

A. Overview

This document describes apparatus, systems, and methods for cooling subcutaneous adipose tissue. The term "subcutaneous tissue" generally refers to tissue lying beneath the dermis and includes subcutaneous fat, or adipose tissue, which primarily is composed of lipid-rich cells, or adipocytes. Several of the details set forth below are provided to describe the following embodiments and methods in a manner sufficient to enable a person skilled in the relevant art to practice, make, and use them. Several of the details and advantages described below, however, may not be necessary to practice certain embodiments and methods of the invention. Additionally, the invention may include other embodiments and methods that are within the scope of the claims but are not described in detail.

Reference throughout this specification to "one embodiment" or "an embodiment" means that a particular feature, structure, or characteristic described in connection with the embodiment is included in at least one embodiment of the present invention. Thus, the occurrences of the phrases "in one embodiment" or "in an embodiment" in various places throughout this specification are not necessarily all referring to the same embodiment. Furthermore, the particular features, structures, or characteristics may be combined in any suitable manner in one or more embodiments. The headings provided herein are for convenience only and do not limit or interpret the scope or meaning of the claimed invention.

B. Suitable Treatment System

Figure 1:
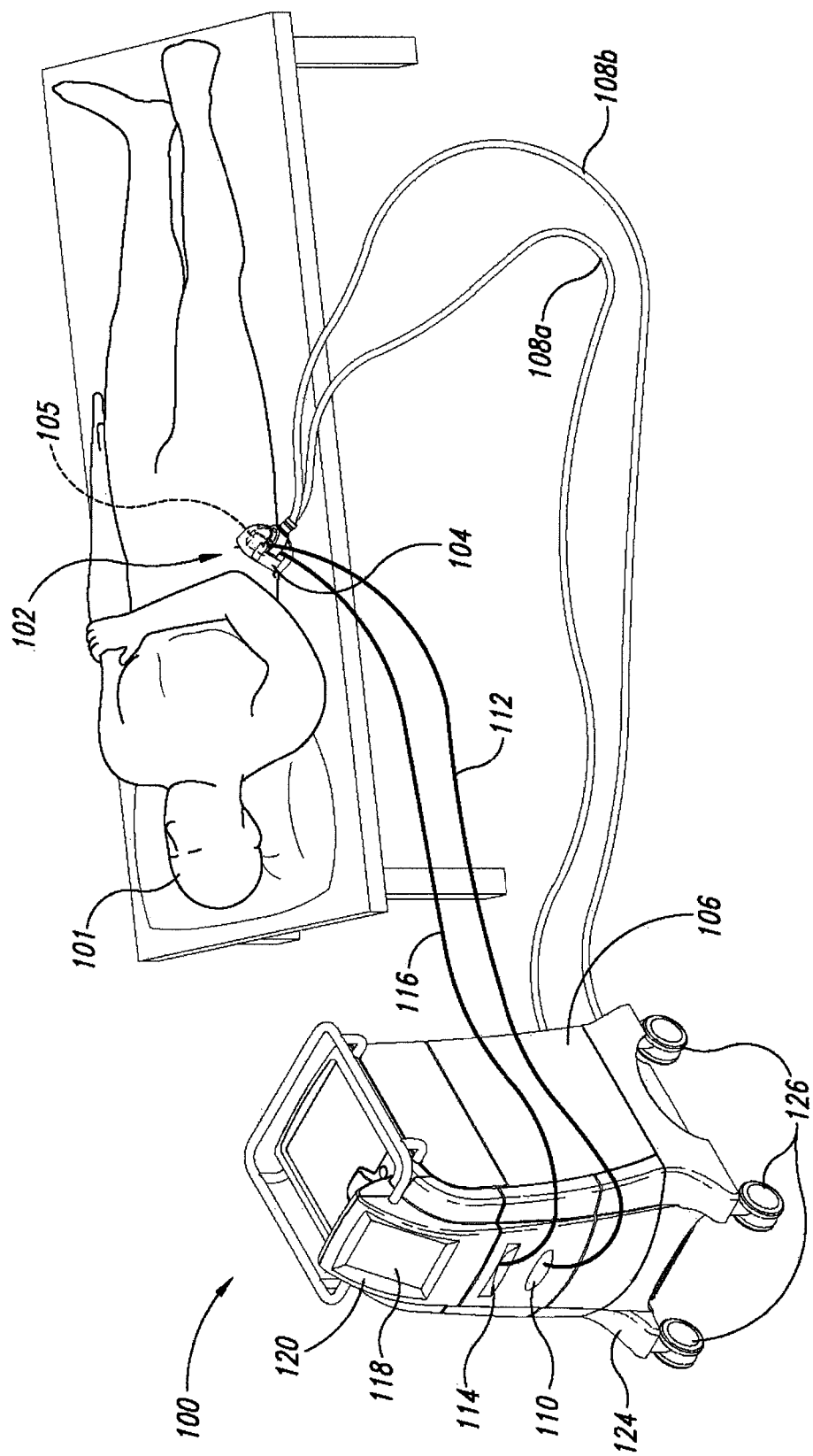
FIG. 1 is an isometric view of a system for treating subcutaneous lipid-rich regions of a subject in accordance with embodiments of the invention.

FIG. 1 and the following discussion provide a brief, general description of a suitable treatment system 100 in which aspects of the disclosure can be implemented. Those skilled in the relevant art will appreciate that the disclosure can be practiced with other treatment systems and treatment protocols, including invasive, minimally invasive, other non-invasive medical treatment systems, and/or combinations of one or more of the above for treating a patient. In general, the term "treatment system", as used generally herein, refers to any of the above system categories of medical treatment as well as any treatment regimes or medical device usage.

The treatment system 100 is suitable for treating a subject's subcutaneous adipose tissue, such as by cooling. The term "subcutaneous tissue" means tissue lying beneath the dermis and includes subcutaneous fat, or adipose tissue, which primarily is composed of lipid-rich cells, or adipocytes. When cooling subcutaneous tissue to a temperature lower than 37° C., subcutaneous lipid-rich cells can selectively be affected, or reduced. In general, the epidermis and dermis of the patient 101 lack lipid-rich cells compared to the underlying lipid-rich cells forming the adipose tissue. Because non-lipid-rich cells usually can withstand colder temperatures better than lipid-rich cells, the subcutaneous lipid-rich cells can selectively be reduced or affected without affecting the non-lipid-rich cells in the dermis, epidermis and other surrounding tissue. In some embodiments, the treatment system 100 can apply cooling temperatures to the skin of the patient in a range of from about −20° C. to about 20° C. In other embodiments, the cooling temperatures can be from about −20° C. to about 10° C., from about 0° C. to about 20° C., from about −15° C. to about 5° C., from about −5° C. to about 15° C., or from about −10° C. to about 0° C.

Without being bound by theory, the selective effect of cooling on lipid-rich cells is believed to result in, for example, membrane disruption, shrinkage, disabling, destroying, removing, killing, or another method of lipid-rich cell alteration. Such alteration is believed to be an intermediate and/or final result of one or more mechanisms acting alone or in combination. It is thought that such mechanism or mechanisms trigger an apoptotic cascade, which is believed to be the dominant form of lipid-rich cell death by non-invasive cooling.

Apoptosis, also referred to as "programmed cell death", is a genetically-induced death mechanism by which cells self-destruct without incurring damage to surrounding tissue. An ordered series of biochemical events induce cells to morphologically change. These changes include cellular blebbing, loss of cell membrane asymmetry and attachment, cell shrinkage, chromatin condensation, and chromosomal DNA fragmentation. Injury via an external stimulus, such as cold exposure, is one mechanism that can induce apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" *Cryobiology* 27, 439-451 (1990).

One aspect of apoptosis, in contrast to cellular necrosis (a traumatic form of cell death causing local inflammation), is that apoptotic cells express and display phagocytic markers on the surface of the cell membrane, thus marking the cells for phagocytosis by, for example, macrophages. As a result, phagocytes can engulf and remove the dying cells (e.g., the lipid-rich cells) without eliciting an immune response. Temperature exposures that elicit these apoptotic events in lipid-rich cells may contribute to long-lasting and/or permanent reduction and reshaping of subcutaneous adipose tissue.

Without being bound by theory, one mechanism of apoptotic lipid-rich cell death by cooling is believed to involve localized crystallization of lipids within the adipocytes at temperatures that do not induce crystallization in non-lipid-rich cells. The crystallized lipids may selectively injure these cells, inducing apoptosis (and may also induce necrotic death if the crystallized lipids damage or rupture the bilayer lipid membrane of the adipocyte). Another mechanism of injury involves the lipid phase transition of those lipids within the cell's bilayer lipid membrane, which results in membrane disruption, thereby inducing apoptosis. This mechanism is well-documented for many cell types and may be active when adipocytes, or lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" *Heart Failure Reviews,* 8, 277-284 (2003). Other yet-to-be understood apoptotic mechanisms may exist, based on the relative sensitivity of lipid-rich cells to cooling compared to non-lipid rich cells.

In addition to the apoptotic mechanisms involved in lipid-rich cell death, local cold exposure may induce lipolysis (i.e., fat metabolism) of lipid-rich cells. For example, cold stress has been shown to enhance rates of lipolysis from that observed under normal conditions which serves to further increase the volumetric reduction of subcutaneous lipid-rich cells. Vallerand, A. L., Zamecnik. J., Jones, P. J. H., Jacobs, I. "Cold Stress Increases Lipolysis, FFA Ra and TG/FFA Cycling in Humans" *Aviation, Space and Environmental Medicine* 70, 42-50 (1999).

In various embodiments, the system 100 includes a controller, a computing device, a data acquisition device, a treatment unit, and one or more applicators. The system can employ these components in various embodiments to receive a selection of a treatment profile and apply the selected treatment using an applicator.

FIG. 1 is an isometric view schematically illustrating the treatment system 100 for non-invasively removing heat from subcutaneous lipid-rich regions of a subject patient 101 in accordance with an embodiment of the disclosure. The system 100 can include a treatment device 104 including an applicator 105 that engages a target region of the subject 101. The treatment device 104 can be placed, for example, at an abdominal area 102 of the Subject 101 or another suitable area for cooling or removing heat from the subcutaneous lipid-rich cells of the subject 101. It will be understood that treatment devices 104 and applicators 105 can be provided having various, configurations, shapes and sizes suitable for different body regions and body parts such that any suitable area for removing heat from a subcutaneous lipid-rich region of the subject 101 can be achieved.

An applicator, such as applicator 105, is a component of the system 100 that cools a region of a subject 101, such as a human or animal (i.e., "patient"). Various types of applicators may be applied during treatment, such as a vacuum applicator, a belt applicator (either of which may be used in combination with a massage or vibrating capability), and so forth. Each applicator may be designed to treat identified portions of the patient's body, such as chin, cheeks, arms, pectoral areas, thighs, calves, buttocks, abdomen, "love handles", back, and so forth. For example, the vacuum applicator may be applied at the back region, and the belt applicator can be applied around the thigh region, either with or without massage or vibration. Exemplary applicators are described in, e.g., commonly assigned U.S. Patent Publication Nos. 2007/0198071, 2008/0077201, 2008/0077211, and 2008/0287839.

In further embodiments, the system 100 may also include a patient protection device (not shown) incorporated into or configured for use with the applicator that prevents the applicator from directly contacting a patient's skin and thereby reducing the likelihood of cross-contamination between patients, minimizing cleaning requirements for the applicator. The patient protection device may also include or incorporate various storage, computing, and communications devices, such as a radio frequency identification (RFID) component, allowing for example, monitoring and/or metering usage as described in U.S. patent application Ser. No. 11/777,992; U.S. patent application Ser. No. 11/777,995, entitled "LIMITING USE OF DISPOSABLE SYSTEM PATIENT PROTECTION DEVICES" to Levinson et al., filed Jul. 13, 2007; U.S. patent application Ser. No. 11/777,999, entitled "MANAGING SYSTEM TEMPERATURE TO REMOVE HEAT FROM LIPID-RICH REGIONS" to Levinson et al., filed Jul. 13, 2007; U.S. patent application Ser. No. 11/778,001, entitled "USER INTERFACES FOR A SYSTEM THAT REMOVES HEAT FROM LIPID-RICH REGIONS" to Levinson et al., filed Jul. 13, 2007; and U.S. patent application Ser. No. 11/778,003, entitled "SECURE SYSTEMS FOR REMOVING HEAT FROM LIPID-RICH REGIONS" to Levinson et al., filed Jul. 13, 2007, the entire disclosures of which are incorporated herein by reference. Exemplary patient protection devices are described in commonly assigned U.S. Patent Publication No. 2008/0077201.

In the present example, the system 100 can further include a treatment unit 106 and supply and return fluid lines 108a-b between the treatment device 104 and the treatment unit 106. A treatment unit 106 is a device that, based on variable power input, can increase or decrease the temperature at a connected treatment device 104 that in turn may be attached to or incorporated into the applicator 105. The treatment unit 106 can remove heat from a circulating coolant to a heat sink and provide a chilled coolant to the treatment device 104 via the fluid lines 108a-b. Alternatively, treatment unit 106 can circulate warm coolant to the treatment device 104 during periods of warming. Examples of the circulating coolant include water, glycol, synthetic heat transfer fluid, oil, a refrigerant, and/or any other suitable heat conducting fluid. The fluid lines 108a-b can be hoses or other conduits constructed from polyethylene, polyvinyl chloride, polyurethane, and/or other materials that can accommodate the particular circulating coolant. The treatment unit 106 can be a refrigeration unit, a cooling tower, a thermoelectric chiller, or any other device capable of removing heat from a coolant. Alternatively, a municipal water supply (e.g., tap water) can be used in place of the treatment unit 106. One skilled in the art will recognize that there are a number of other cooling technologies that could be used such that the treatment unit or chiller need not be limited to those described herein.

In this example, the treatment device 104 includes at least one applicator 105 and at least one treatment unit 106. The applicator 105 can provide mechanical energy to create a vibratory, massage, and/or pulsatile effect. The applicator 105 can include one or more actuators, such as, motors with eccentric weight, or other vibratory motors such as hydraulic motors, electric motors, pneumatic motors, solenoids, other mechanical motors, piezoelectric shakers, and so on, to provide vibratory energy to the treatment site. Further examples include a plurality of actuators for use in connection with a single treatment device 104 and/or applicator 105 in any desired combination. For example, an eccentric weight actuator can be associated with one treatment device 104 or applicator 105, while a pneumatic motor can be associated with another section of the same treatment device or applicator. This, for example, would give the operator of the treatment system 100 options for differential treatment of lipid rich cells within a single region or among multiple regions of the subject 101. The use of one or more actuators and actuator types in various combinations and configurations with a treatment device 104 or applicator 105 may be possible.

The treatment device 104 can include one or more heat exchanging units. The heat exchanging unit can be a Peltier-type thermoelectric element, and the treatment device 104 can have multiple individually controlled heat exchanging units (e.g., between 1 and 50, between 10 and 45; between 15 and 21, approximately 100, etc.) to create a custom spatial cooling profile and/or a time-varying cooling profile. Each custom treatment profile can include one or more segments, and each segment can include a specified duration, a target heat flux or temperature, and control parameters for features such as vibration, massage, vacuum, and other treatment modes. Treatment devices having multiple individually controlled heat exchanging units are described in commonly assigned U.S. Patent Publication No. 2008/0077211. Embodiments of a treatment device 104 usable with the treatment system 100 are described in more detail below with reference to FIG. 2.

The system 100 can further include a power supply 110 and a controller 114 operatively coupled to the treatment device 104 and the applicator 105. In one embodiment, the power supply 110 can provide a direct current voltage to the thermoelectric treatment device 104 and/or the applicator 105 to remove heat from the subject 101. The controller 114 can monitor process parameters via sensors (not shown) placed proximate to the treatment device 104 via a control line 116 to, among other things, adjust the heat removal rate based on the process parameters. The controller 114 can further monitor process parameters to adjust the applicator 105 based on treatment parameters, such as treatment parameters defined in a custom treatment profile or patient-specific treatment plan.

The controller 114 can exchange data with the applicator 105 via an electrical line 112 or, alternatively, via a wireless or an optical communication link. Note that control line 116 and electrical line 112 are shown in FIG. 1 without any support structure. Alternatively, control line 116 and electrical line 112 (and other lines including, but not limited to fluid lines 108a-b) may be bundled into or otherwise accompanied by a conduit or the like to protect such lines, enhance ergonomic comfort, minimize unwanted motion (and thus potential inefficient removal of heat from subject 101), and to provide an aesthetic appearance to system 100. Examples of such a conduit include a flexible polymeric, fabric, or composite sheath, an adjustable arm, etc. Such a conduit (not shown) may be designed (via adjustable joints, etc.) to "set" the conduit in place for the treatment of subject 101.

The controller 114 can include any processor, Programmable Logic Controller, Distributed Control System, secure processor, and the like. A secure processor can be implemented as an integrated circuit with access-controlled physical interfaces; tamper resistant containment; means of detecting and responding to physical tampering; secure storage; and shielded execution of computer-executable instructions. Some secure processors also provide cryptographic accelerator circuitry. Secure storage may also be implemented as a secure flash memory, secure serial EEPROM, secure field programmable gate array, or secure application-specific integrated circuit.

In another aspect, the controller 114 can receive data from an input device 118 (shown as a touch screen), transmit data to an output device 120, and/or exchange data with a control panel (not shown). The input device 118 can include a keyboard, a mouse, a stylus, a touch screen, a push button, a switch, a potentiometer, a scanner, or any other device suitable for accepting user input. The output device 120 can include a display or touch screen, a printer, a medium reader, an audio device, any combination thereof, and any other device or devices suitable for providing user feedback. In the embodiment of FIG. 1, the output device 120 is a touch screen that functions as both an input device 118 and an output device 120. The control panel can include visual indicator devices or controls (e.g., indicator lights, numerical displays, etc.) and/or audio indicator devices or controls. The control panel may be a component separate from the input device 118 and/or output device 120, may be integrated with one or more of the devices, may be partially integrated with one or more of the devices, may be in another location, and so on. In alternative examples, the control panel, input device 118, output device 120, or parts thereof (described herein) may be contained in, attached to, or integrated with the treatment device 104 and/or applicator 105. In this example, the controller 114, power supply 110, control panel, treatment unit 106, input device 118, and output device 120 are carried by a rack 124 with wheels 126 for portability. In alternative embodiments, the controller 114 can be contained in, attached to, or integrated with the treatment device 104 and/or the applicator 105 and/or the patient protection device described above. In yet other embodiments, the various components can be fixedly installed at a treatment site. Further details with respect to components and/or operation of treatment device 104, treatment unit 106, applicator 105 and other components may be found, for example, in commonly-assigned U.S. Patent Application Publication Nos. 2008/0287839 and 2008/0077201.

In operation, and upon receiving input to start a treatment protocol, the controller 114 can cause the applicator 105 to cycle through each segment of a prescribed treatment plan. In so doing, the applicator 105 applies power to one or more treatment devices 104, such as thermoelectric coolers (e.g., TEC "zones"), to begin a cooling or heating cycle and, for example, activate features or modes such as vibration, massage, vacuum, etc. Using sensors (not shown) proximate to the one or more treatment devices 104, the patient's skin, a patient protection device, or other locations or combinations thereof, the controller 114 determines whether a temperature or heat flux that is sufficiently close to the target temperature or heat flux has been reached. It will be appreciated that while a region of the body (e.g., adipose tissue) has been cooled or heated to the target temperature or by a target heat flux, in actuality that region of the body may be close but not equal to the target temperature, e.g., because of the body's natural heating and cooling variations. Thus, although the system may attempt to heat or cool to the target temperature or by a target heat flux, a sensor may measure a sufficiently close temperature. If the target temperature has not been reached, power can be increased or decreased to change heat flux, as needed, to maintain the target temperature. When the prescribed segment duration expires, the controller 114 may apply the treatment parameters (e.g., heat flux or duration) indicated in the next treatment profile segment. In some embodiments, heat flux or temperature can be controlled using a variable other than, or in addition to, power.

During treatment, the treatment process may be interrupted. As used herein, the word "interrupted" generally refers to being in a state in which the treatment process may not safely and/or effectively proceed. For example, the treatment process may be interrupted when the applicator 105 is detached from the patient. In another example, the treatment process may be interrupted when the sensors (not shown) indicate freezing of the adipose tissue or when the treatment quality is unsatisfactory. In a further example, an operator or the patient may pause the treatment process using, e.g., the input device 118. In yet further examples, the treatment process may be interrupted based on other suitable conditions.

The interrupted treatment may cause operational difficulties and/or safety concerns for the patient. For example, if the operator restarts the treatment process from the initial stages of the treatment plan, the additional cooling or heating may be excessive to injure the adipose tissue of the patient. If the operator simply continues the treatment process, the adipose tissue of the patient may be insufficiently cooled or heated because of blood circulation and/or other physiological activities of the patient during the period of treatment interruption. As a result, the treatment process may not achieve the desired effect. Several embodiments of the treatment system 100 can at least reduce the impact of such interruptions by monitoring for an interruption and performing a recovery process to compensate for the interruption, as described in more detail below with reference to FIGS. 4-8.

Although a noninvasive applicator is illustrated and discussed herein, minimally invasive applicators may also be employed in connection with a noninvasive applicator. In such a case, the applicator and patient protection device may be integrated. As an example, a cryoprobe that may be inserted directly into the subcutaneous adipose tissue to cool or freeze the tissue is an example of such a minimally invasive applicator. Cryoprobes manufactured by, e.g., Endocare, Inc., of Irvine, Calif. are suitable for such applications. This patent application incorporates by reference U.S. Pat. No. 6,494,844, entitled "DEVICE FOR BIOPSY AND TREATMENT OF BREAST TUMORS"; U.S. Pat. No. 6,551,255, entitled "DEVICE FOR BIOPSY OF TUMORS"; U.S. Patent Publication No. 2007/0055173, entitled "ROTATIONAL CORE BIOPSY DEVICE WITH LIQUID CRYOGEN ADHESION PROBE"; U.S. Pat. No. 6,789,545, entitled "METHOD AND SYSTEM FOR CRYOABLATING FIBROADENOMAS"; U.S. Patent Publication No. 2004/0215294, entitled "CRYOTHERAPY PROBE"; U.S. Pat. No. 7,083,612, entitled "CRYOTHERAPY SYSTEM"; U.S. Patent Publication No. 2005/0261753, entitled "METHODS AND SYSTEMS FOR CRYOGENIC COOLING", and U.S. patent application Ser. No. 11/933,066, entitled "METHOD AND APPARATUS FOR COOLING SUBCUTANEOUS LIPID-RICH CELLS OR TISSUE" to Ebbers et al., filed Oct. 31, 2007.

Figure 2:
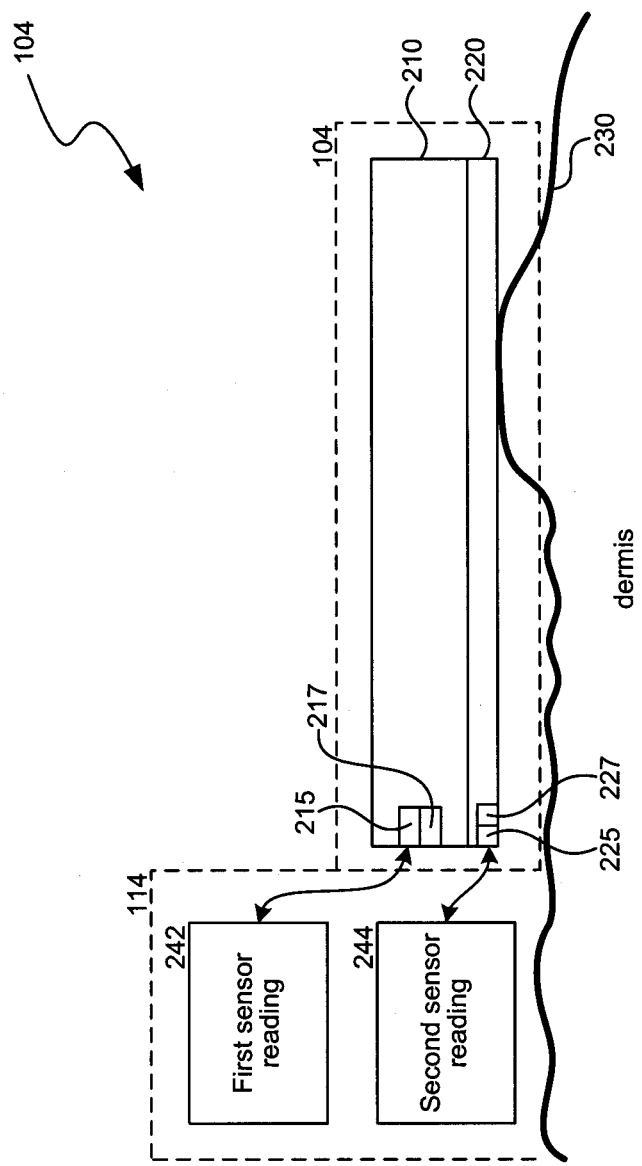
FIG. 2 is a partial cross-sectional view illustrating a treatment device suitable to be used in the system of FIG. 1 in accordance with embodiments of the invention.

FIG. 2 is a schematic diagram illustrating the treatment device 104 for removing heat from subcutaneous lipid-rich cells in accordance with one embodiment. The treatment device 104 may include a heat exchanging unit, such as a heat exchanging plate 210, and an interface layer 220. The interface layer 220 may be a plate, a film, a covering, or other suitable materials described herein and may serve as the patient protection device described herein. The interface layer 220 is located between the heat exchanging plate 210 and the skin 230 of a subject (not shown), such as the skin of a patient receiving treatment via the treatment device 104. The heat exchanging plate 210 may contain a communication component 215 that communicates with the controller 114 to provide a first sensor reading 242 as described herein, and a sensor 217 that measures, e.g., the temperature of the heat exchanging plate 210 or heat flux across a surface of or plane within the heat exchanging plate 210. The interface layer 220 may also contain a similar communication component 225 that communicates with the controller 114 to provide a second sensor reading 244 and a sensor 227 that measures, e.g., the temperature of the interface layer 220 or heat flux across a surface of or plane within the interface layer 220. For example, one or both of communication components 215, 225 may receive and transmit information from the controller 114, such as temperature and/or heat flux information as determined by one or both of the sensors 217, 227. The treatment device 104 may also contain power components and other components described with respect to FIG. 1 and related applications.

In certain embodiments, the interface layer 220 of the treatment device 104 may include a sleeve for contacting the patient's skin 230. The sleeve may include a first sleeve portion (not shown) and a second sleeve portion (not shown) extending from the first sleeve portion. The first sleeve portion may contact and/or facilitate the contact of the treatment device 104 with the patient's skin 230. The second sleeve portion may be an isolation layer extending from the first sleeve portion. The second sleeve portion may be constructed from latex, rubber, nylon, Kevlar®, or other substantially impermeable or semi-permeable material. The second sleeve portion may prevent contact between the patient's skin 230 and the heat exchanging plates, among other things. Further details regarding a suitable sleeve may be found in U.S. Patent Publication No. 2008/0077201.

In other embodiments, the treatment device 104 may include a belt that assists in forming a contact between the treatment device 104 (such as via an interface layer 220) and the patient's skin 230. For example, the treatment device 104 may include retention devices (not shown) coupled to a frame. The retention devices may be rotatably connected to the frame by a plurality of coupling elements that may be, for example, pins, ball joints, bearings, or other type of rotatable joints. Alternatively, the retention devices may be rigidly affixed to the end portions of heat exchanging element housings. Further details regarding a suitable belt device may be found in U.S. Patent Publication No. 2008/0077211.

In further embodiments, the treatment device 104 may include a vacuum (not shown) that assists in forming a contact between the treatment device 104 (such as via the interface layer 220) and the patient's skin 230. For example, the treatment device 104 may provide mechanical energy to a treatment region. Imparting mechanical vibratory energy to the patient's tissue by repeatedly applying and releasing a vacuum to the subject's tissue, for instance, creates a massage action during treatment. Further details regarding a vacuum type device may be found in U.S. Patent Application Publication No. 2008/0287839.

C. Computing System Software Modules

Figure 3:
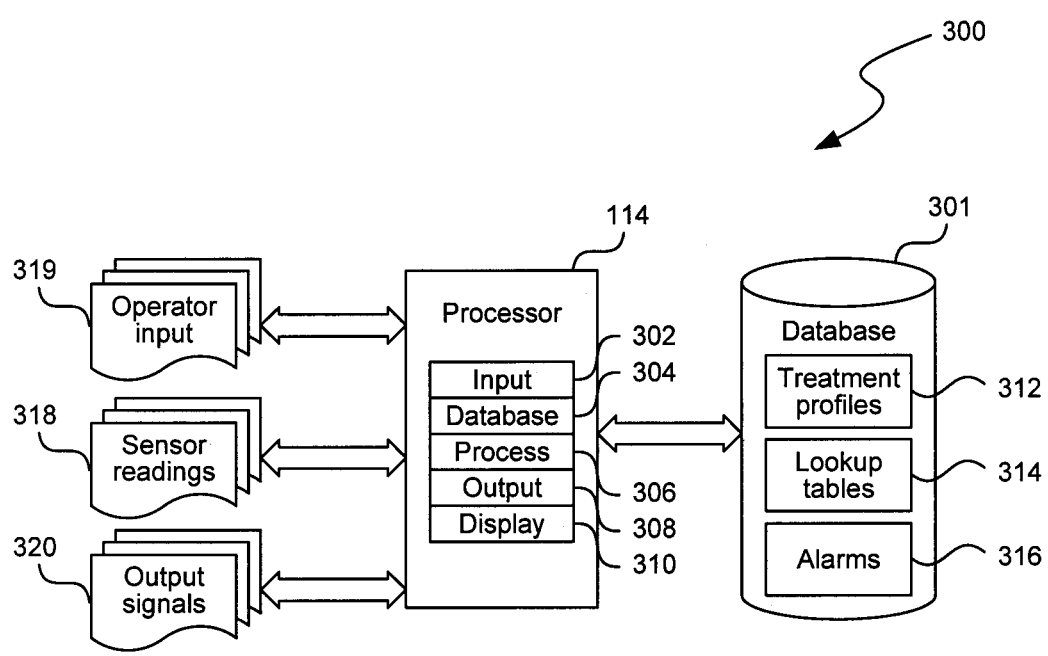
FIG. 3 is a block diagram showing computing system software modules for removing heat from subcutaneous lipid-rich cells in accordance with embodiments of the invention.

FIG. 3 is a functional diagram showing software modules 300 suitable for use in the controller 114 of FIG. 1. Each component may be a computer program, procedure, or process written as source code in a conventional programming language, such as C, C+, C++, C# etc., and may be presented for execution by a CPU of the controller 114. The various implementations of the source code and object byte codes may be stored on a computer-readable storage medium. The modules of controller 114 may include an input module 302, a database module 304, a process module 306, an output module 308, and, optionally, a display module 310 interconnected with one another.

In operation, the input module 302 accepts an operator input 319, such as process setpoint (e.g., a target heat flux or temperature) and control selections (e.g., a resume/terminate selection), and communicates the accepted information or selections to other components for further processing. The database module 304 organizes records, including treatment profiles 312, lookup tables 314, and alarms 316, and facilitates storing and retrieving of these records to and from a database 301. The treatment profiles 312 may include various therapies for treating different areas of the subject 101 (FIG. 1). For example, the treatment profiles 312 may include a pre-cooling duration, a steady state duration, a termination duration, and/or other suitable parameters for a treatment process. The lookup tables 314 may include values of temperatures of adipose tissue and corresponding time of cooling or warming. Any type of database organization may be utilized, including a flat file system, hierarchical database, relational database, or distributed database, such as provided by a database vendor such as Oracle Corporation, Redwood Shores, Calif.

The process module 306 generates control variables based on sensor readings 318 from sensors (e.g., the temperature measurement components 217 and 227 of FIG. 2) and/or other data sources, and the output module 308 generates output signals 320 based on the control variables. The controller 114 optionally may include the display module 310 for displaying, printing, or downloading the sensor readings 318, output signals 320, and/or other information via devices such as the output device 120 (FIG. 1). A suitable display module 310 may include a video driver that enables the controller 114 to display the sensor readings 318 or other status of treatment resumption on the output device 120.

Figure 4:
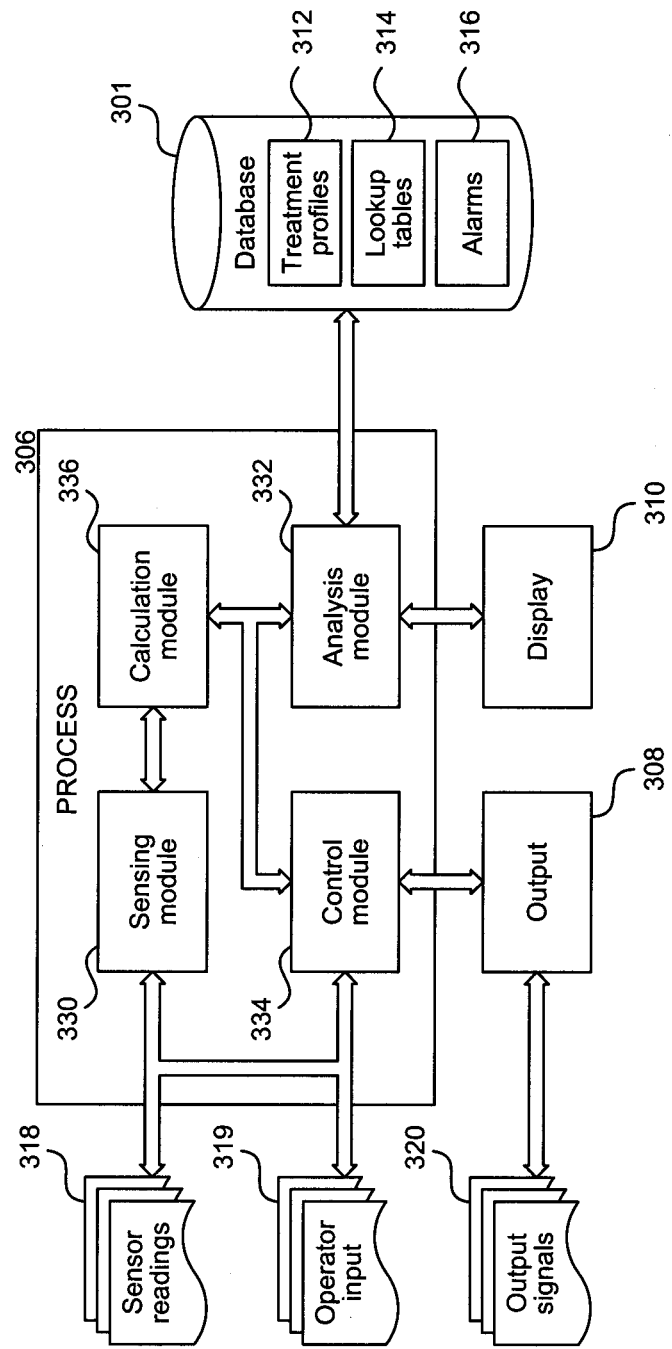
FIG. 4 is a block diagram showing a process module suitable to be used in the computing system of FIG. 3.

FIG. 4 is a block diagram showing an embodiment of the process module 306 of FIG. 3. The process module 306 may further include a sensing module 330, an analysis module 332, a control module 334, and a calculation module 336 interconnected with one other. Each module may be a computer program, procedure, or routine written as source code in a conventional programming language, or one or more modules may be hardware modules.

The sensing module 330 is configured to receive and convert the sensor readings 318 into parameters in desired units. For example, the sensing module 330 may receive the sensor readings 318 as electrical signals (e.g., a voltage or a current) and convert the electrical signals into instant temperatures in Celsius. In another example, the sensing module 330 may convert the electrical signals into an oxygen depletion level in the treated area as an indicator of hypoxia or ischemia. The sensing module 330 may have routines including, for example, linear interpolation, logarithmic interpolation, data mapping, or other routines to associate the sensor readings 318 to parameters in desired units.

The calculation module 336 may include routines configured to perform various types of calculation to facilitate operation of other modules. For example, the calculation module 336 may include counters, timers, and/or other suitable accumulation routines for deriving an elapsed time of treatment (t), an elapsed time since an interruption (τ), and/or other parameters associated with the interruption. Further, the calculation module 336 may include routines configured to calculate tissue temperatures at different times during treatment based on temperature parameters, heat flux parameters, and/or other suitable parameters.

In certain embodiments, the calculation module 336 may also include a computation routine for deriving an interruption temperature ($T_{interrupt}$) of the adipose tissue based on the measured temperatures from at least one of the sensors 217 and 227 according to the following formula:

$$T_{interrupt} = T_o e^{-kt} \quad \text{(Equation I)}$$

where $T_o$ is an initial temperature of the adipose tissue (e.g., 37° C.) and k is a time constant associated with cooling the adipose tissue. The cooling time constant k may be empirically derived for a particular interface temperature (e.g., 0° C.) between the cooling plate 210 (FIG. 2) and the skin 230 of the subject 101 (FIG. 2) by performing an exponential curve fitting on a tissue temperature versus time plot (e.g., the plot shown in FIG. 7) and/or other suitable techniques. Equation I may also be used to derive an instant temperature of the adipose tissue during cooling.

In other embodiments, the calculation module 336 may also include another computation routine for deriving a rewarming temperature ($T_{rewarm}$) of the adipose tissue after the interruption according to the following formula:

$$T_{rewarm} = T_{interrupt} e^{-m\tau} \quad \text{(Equation II)}$$

where m is a time constant associated with rewarming the adipose tissue. The rewarming time constant m may also be empirically derived for a particular ambient temperature (e.g., 25° C.) by performing an exponential curve fitting on a tissue temperature versus time plot (e.g., the plot shown in FIG. 8) and/or other suitable techniques.

Figure 7:
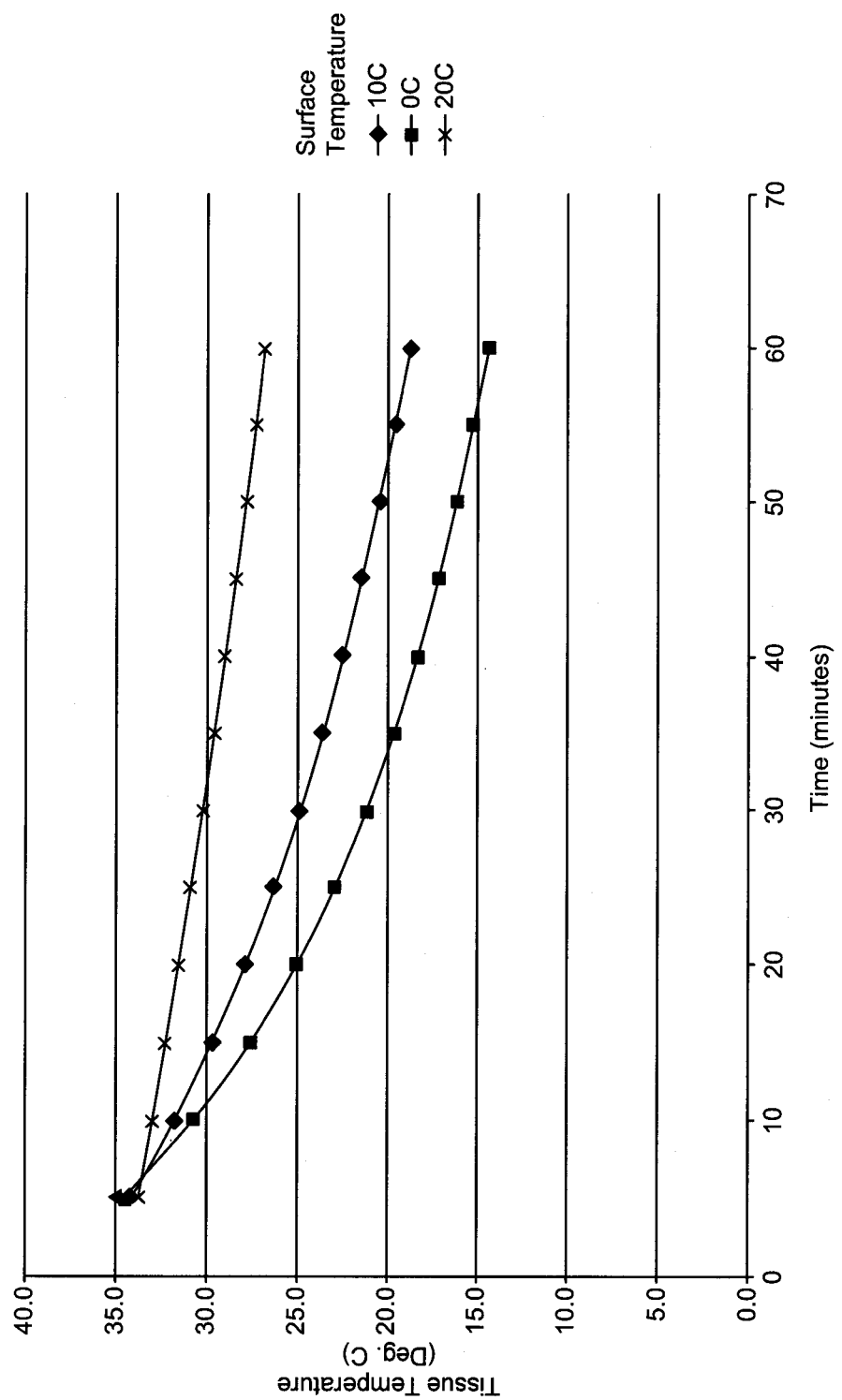
FIG. 7 is an example of a tissue temperature versus time plot during cooling adipose tissue.
Figure 8:
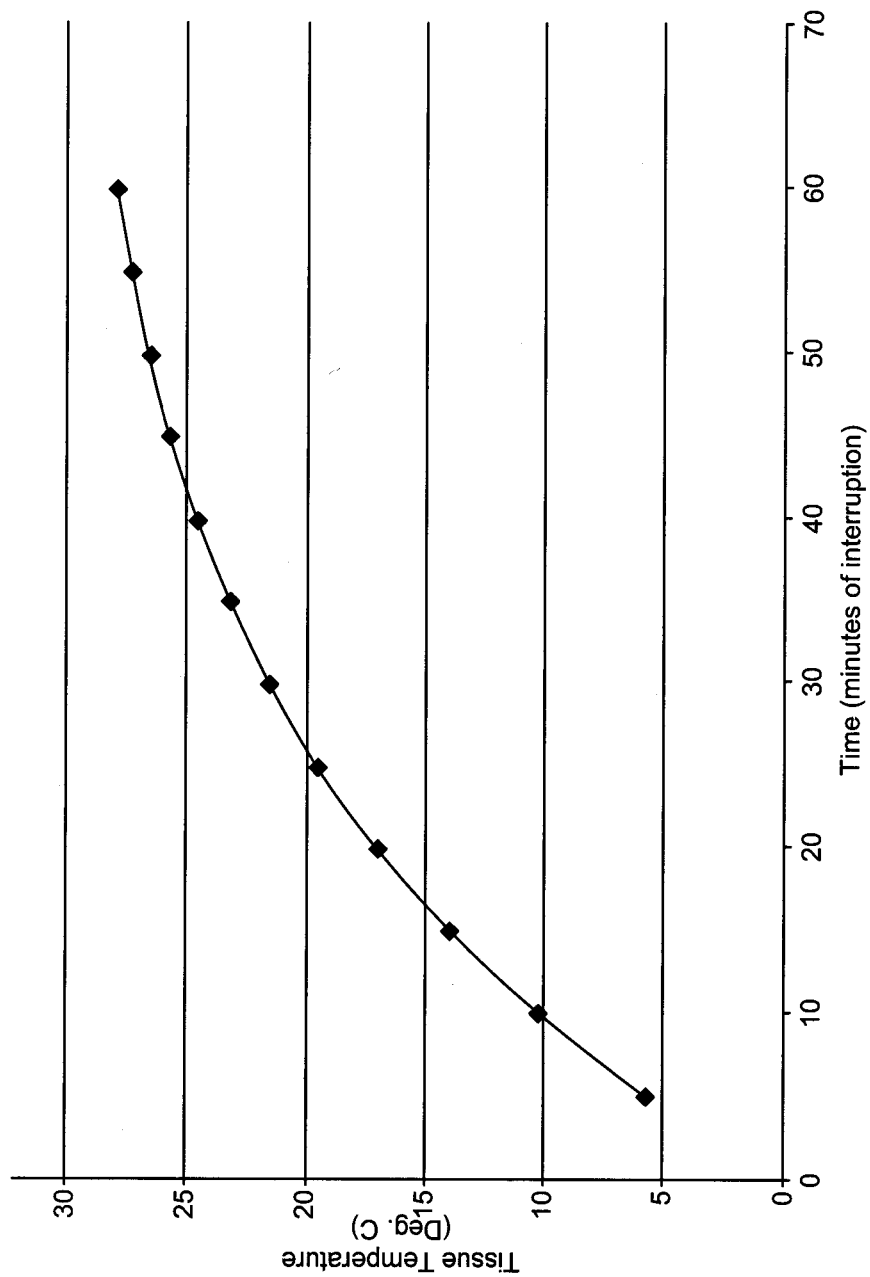
FIG. 8 is an example of a tissue temperature versus time plot during rewarming adipose tissue.

In further embodiments, the calculation module 336 may include a lookup routine to derive the interruption temperature ($T_{interrupt}$) and/or the rewarming temperature ($T_{rewarm}$) of the adipose tissue based on the lookup tables 314 stored in the database 301 or plots of temperature versus time for cooling and/or rewarming of the adipose tissue. Examples of such temperature versus time plots for cooling and rewarming are shown in FIGS. 7 and 8, respectively.

In yet further embodiments, thermal modeling of different tissue and/or applicator geometries may result in different equations for deriving the interruption temperature of Equation I ($T_{interrupt}$) and/or the rewarming temperature of Equation II ($T_{rewarm}$). Moreover, even though the foregoing description is directed toward a process for cooling the adipose tissue, in other embodiments, the calculation module 336 may also include other suitable computation routines for calculating the interruption temperature and/or other parameters of the adipose tissue during a process for heating, or a combination of heating and cooling the adipose tissue.

In yet further embodiments, the calculation module 336 may also be configured to derive a rate of change for the interface temperature according to the following formula:

$$\frac{dT}{dt} \approx \frac{T_{i+1} - T_i}{\Delta t} \quad \text{(Equation III)}$$

where $T_{i+1}$ is the temperature record number i+1, $T_i$ is the previous temperature record, and $\Delta t$ is the time difference between the two temperature records. The calculation module 336 may be configured to derive a rate of change of the temperature of the adipose tissue in a similar fashion.

The calculation module 336 may also be configured to derive a profile for a recovery process in response to the interruption. For example, the calculation module 336 may include a computation routine for calculating an amount of heat (Q) that must be removed from the adipose tissue to return the adipose tissue to the temperature at the time of the interruption as follows:

$$Q = \rho V C_P (T_{rewarm} - T_{interrupt}) \quad \text{(Equation IV)}$$

where ρ is the density of the adipose tissue (e.g., about 918 kg/m³); V is a volume of the adipose tissue that approximately corresponds to a cross-sectional area of the cooling plate 210 and a thickness of the adipose tissue (e.g., about 0.1 m to about 0.2 m); and $C_P$ is the specific heat capacity of the adipose tissue (e.g., about 3.5 kJ/kg ° C.).

The density and specific heat capacity of the adipose tissue may empirically be determined. In certain embodiments, the operator may adjust the thickness of the adipose tissue, select a value from a list of available options, or enter a value determined by direct measurement involving, for example, ultrasound, calipers, electrical conductance, etc. In other embodiments, the thickness of the adipose tissue may automatically be set based on a particular treatment area (e.g., thighs, buttocks, etc.)

The calculation module 336 may also include another computation routine for deriving a desired cooling rate ($\dot{Q}$) for the recovery process as follows:

$$\dot{Q} = \frac{Q}{\pi} = \frac{\rho V C_p (T_{rewarm} - T_{interrupt})}{\pi} \quad \text{(Equation V)}$$

where π is a recovery duration. In certain embodiments, the operator may set the recovery duration (π) to any desired value with or without bounds. In other embodiments, the recovery duration (π) may be preselected and inaccessible to the operator.

In certain embodiments, the calculation module 336 may further include a computation routine for calculating an expected average rate of change in the temperature of the adipose tissue during the recovery period as follows:

$$\Delta T = \frac{(T_{rewarm} - T_{interrupt})}{\pi}$$ (Equation VI)

In other embodiments, the expected rate of change may also be based on the interface temperature between the cooling plate 210 and the skin 230 of the subject 101.

The analysis module 332 may be configured to analyze parameters from the sensing module 330 and the calculation module 336 and to determine (1) whether an interruption has occurred; and (2) whether the treatment process may be resumed. The display module 310 may then receive the determined results for output to the operator. In certain embodiments, the analysis module 332 may indicate an interruption when the following conditions occur:

The input module 302 (FIG. 3) receives an interruption indication from the operator and/or the subject 101.

The calculated rate of change for the measured skin temperature is above (or below) a threshold (e.g., 0.1° C./sec), or alternatively, the measured heat flux across the skin is above (or below) a threshold (e.g., 50 mW/cm$^2$).

The measured bio-resistance of the skin 230 of the subject 101 is above a threshold.

In other embodiments, the analysis module 332 may indicate an interruption based on other suitable conditions. In further embodiments, the analysis module 332 can also generate an alarm after an interruption is indicated and store the alarm in the database 301 as alarms 316.

The analysis module 332 may also be configured to determine whether the treatment process may be resumed based on the following conditions:

If the elapsed time since the interruption ($\tau$) is not less than a difference between the elapsed time of treatment (t) and a preselected ramp time (A) as follows:

$\tau \geq (t-A)$, the analysis module 332 indicates that the process cannot be resumed. In one embodiment, the preselected ramp time (A) may be the time required to cool the interface layer 220 to a desired treatment temperature. In other embodiments, the preselected ramp time (A) may have other desired values; or If the elapsed time since the interruption ($\tau$) is greater than a preselected maximum interruption time (B) as follows:

$\tau \geq B$;

the analysis module 332 indicates that the process cannot be resumed. In one embodiment, the maximum interruption time (B) may have a value at which the adipose tissue would have been sufficiently rewarmed (e.g., 10 minutes). In other embodiments, the maximum interruption time (B) may have other desired values; or If the treatment process has been interrupted for more than a preselected number of occurrences (e.g., 2 times), the analysis module 332 indicates that the process cannot be resumed.

In other embodiments, the analysis module 332 may indicate that the process cannot be resumed based on other suitable conditions.

The control module 334 may be configured to determine whether the recovery process should be initiated. In one embodiment, if the analysis module 332 indicates that an interruption has occurred and the treatment process may be resumed, the control module 334 may automatically initiate the recovery process. In another embodiment, the display module 310 may output the result from the analysis module 332 and prompt the operator for input. The input module 302 (FIG. 3) may accept and then transmit the operator input 319 to the control module 334 for determining whether to initiate the recovery process or terminate the treatment process. In further embodiments, the control module 334 can determine whether to initiate the recovery process based on other suitable conditions.

The control module 334 may also be configured to monitor parameters of the recovery process and adjust the recovery process based on the monitored parameters. In one embodiment, the control module 334 may monitor a rate of change of the temperature of the adipose tissue and/or the interface temperature during the recovery process. If the monitored rate of change is below the expected rate of change from Equation VI by a preselected amount (e.g., 25%), then the control module 334 may (1) increase a power output to the cooling plate 210 by a preselected amount or by a proportional-derivative-integral (PID) routine using the rate of change as a process variable; and/or (2) increase the recovery duration by a preselected amount (e.g., 3 minutes); otherwise, the control module 334 continues to monitor the recovery process. In other embodiments, the control module 334 may also monitor a heat flux, a thermal image, and/or other parameters of the recovery process.

D. Treatment Resumption Methods

Figure 5:
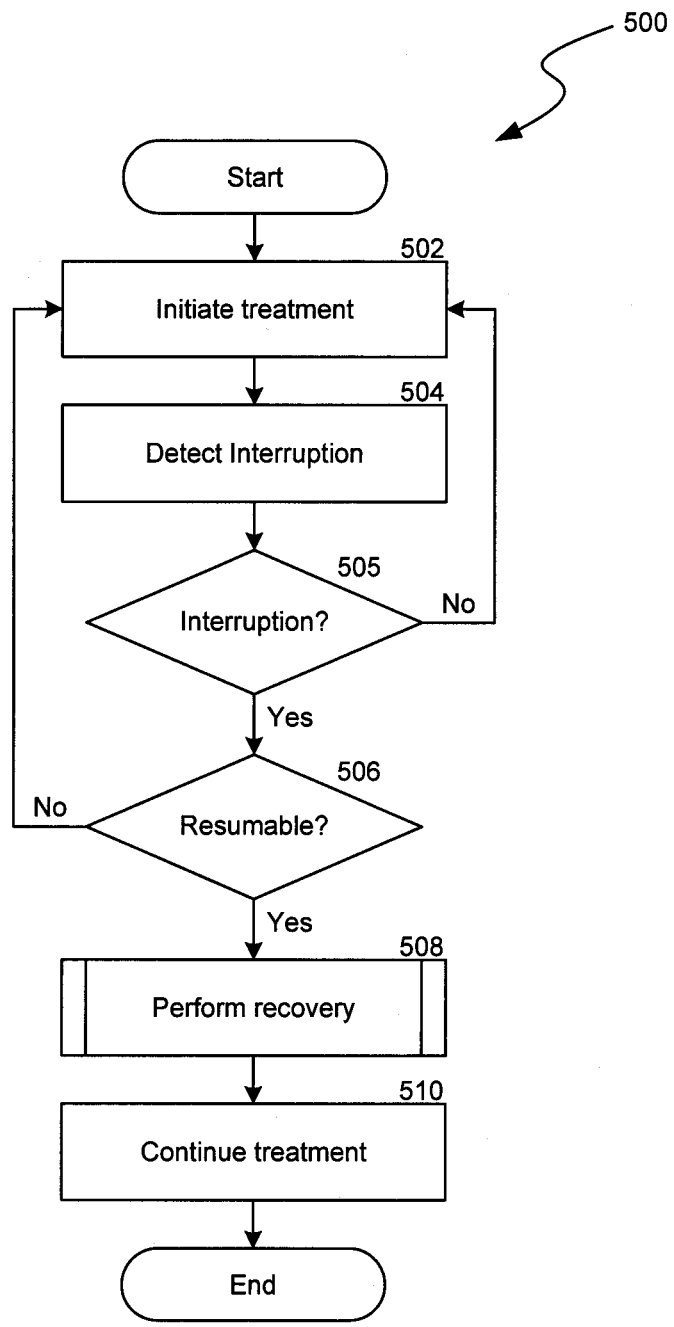
FIG. 5 is a flow diagram showing a method for treating subcutaneous lipid-rich regions of a subject in accordance with embodiments of the invention.

FIG. 5 is a flow diagram illustrating a method 500 for treating subcutaneous lipid-rich regions of a subject in accordance with embodiments of the invention. Even though the method 500 is described below with reference to the treatment system 100 of FIG. 1, the treatment device 104 of FIG. 2, and the software modules of FIGS. 3 and 4, the method 500 may also be applied in other treatment systems with additional or different hardware and/or software components.

As shown in FIG. 5, an early stage 502 of the method 500 may include initiating a treatment process for the subject. In one embodiment, initiating the treatment process may include receiving an initiation input with the input module 302 via, for example, the input device 118 and retrieving a suitable treatment profile from the database 301. Then the control module 334 may activate the treatment device 104 and/or other components of the treatment system 100 to remove heat from the skin 230 of the subject 101 (FIG. 2) according to the retrieved treatment profile. The calculation module 336 may accumulate the elapsed time of treatment by, for example, activating an internal timer or counter.

Another stage 504 of the method 500 may include detecting an interruption in the treatment process. In one embodiment, detecting the interruption may include accepting an input for pause from the operator and/or the subject 101 by the input module 302. In other embodiments, detecting an interruption may include continuously sensing an interface temperature between the cooling plate 210 and the skin 230 of the subject 101 with the sensing module 330, calculating a rate of change for the sensed temperature with the calculation module 336, and analyzing the calculated rate of change of the sensed temperature with the analysis module 332. In further embodiments, detecting an interruption may include detecting skin freezing, monitoring treatment quality, identifying movement of the treatment device 104 (FIG. 1), as described in commonly assigned U.S. patent application Ser. No. 12/196,246 entitled "MONITORING THE COOLING OF SUBCUTANEOUS LIPID-RICH CELLS, SUCH AS THE COOLING OF ADIPOSE TISSUE," filed Aug. 21, 2008, the disclosure of which is incorporated by reference in its entirety.

A determination is made at stage 505. If an interruption is not detected, the process reverts to continuing the treatment process at stage 502. If an interruption is detected, the process continues to another stage 506 for determining with the analysis module 332 whether the treatment process may be resumed. The calculation module 336 may then determine the accumulated elapsed time of treatment and accumulate the elapsed time of interruption by, for example, activating another internal timer or counter. If the treatment process may not be resumed, the process reverts to initiating another treatment process at stage 502, and the calculation module 336 may reset both the elapsed time of treatment and the elapsed time of interruption.

If the treatment process is determined to be resumable, in one embodiment, the method 500 includes another stage 508 in which a recovery process is performed in response to the interruption. Optionally, in another embodiment, the interruption and the determination that the treatment process may be resumed can be indicated to the operator via, e.g., the display 118 (FIG. 1). The operator may choose to proceed with the recovery process or terminate the treatment process.

In one embodiment, performing the recovery process includes returning the adipose tissue to a condition (e.g., temperature) at least approximately equal to that at the time of the interruption. In other embodiments, if the interruption is detected based on tissue freezing, tissue overheating, and/or other suitable conditions, the adipose tissue may not be returned to a condition at least approximately equal to that at the time of interruption. Instead, performing the recovery process may include cooling, warming, and/or otherwise treating the adipose tissue and/or surrounding tissue based on suitable parameters to reduce the likelihood of injury. In yet other embodiments, performing the recovery process may include replacing the interface layer 220 with a new piece and pre-cooling the new interface layer 220 to a suitable temperature. Several embodiments of performing the recovery process are described in more detail below with reference to FIG. 6.

After performing the recovery process at stage 508, the method 500 may also include continuing the interrupted treatment process at stage 510. In one embodiment, continuing the interrupted treatment process includes performing the remaining treatment operations according to the treatment profile. For example, if the treatment profile includes cooling the skin 230 of the subject 101 for a total of 30 minutes, and the elapsed treatment time is 10 minutes, continuing the interrupted treatment process includes cooling the skin 230 of the subject 101 for another 20 minutes after performing the recovery process. In other embodiments, continuing the interrupted treatment process may also include performing other suitable operations according to the treatment profile.

Figure 6:
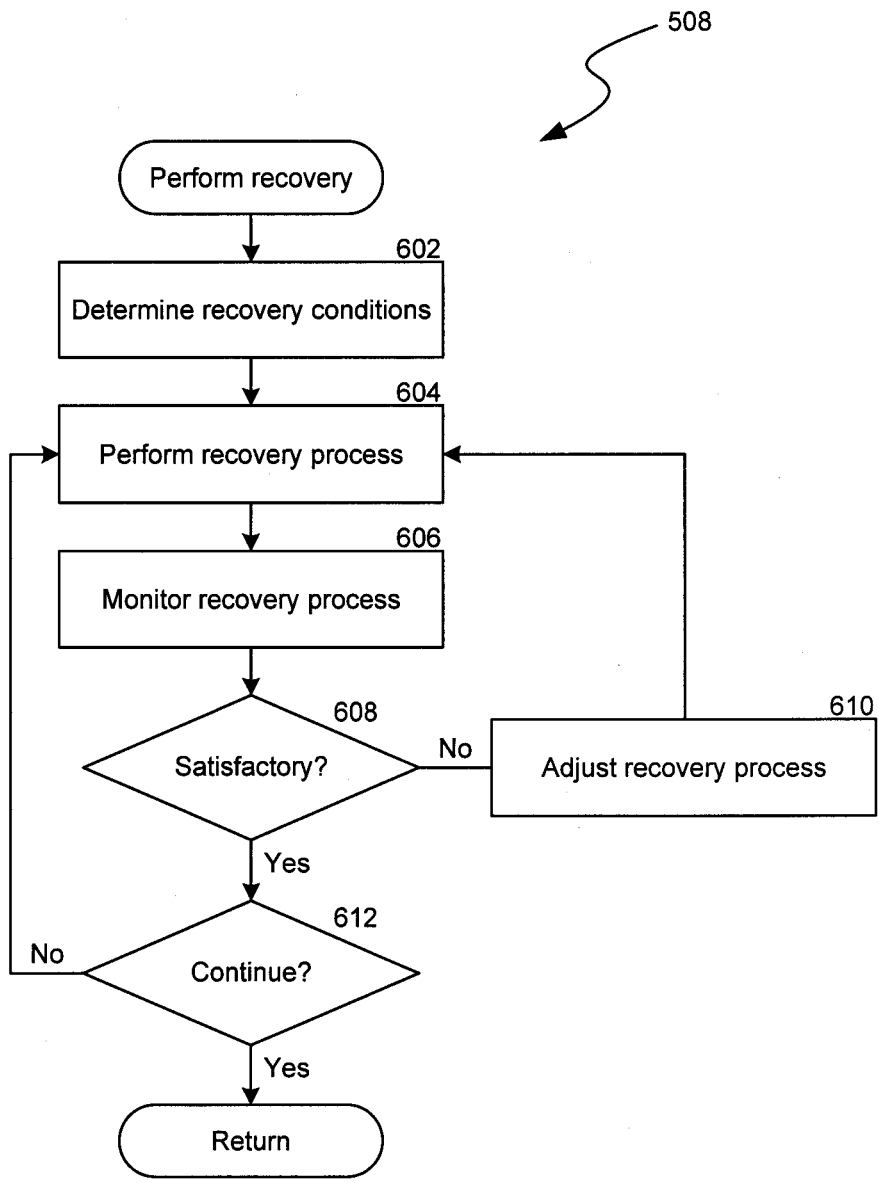
FIG. 6 is a flow diagram showing a method for performing a recovery process in accordance with embodiments of the invention.

FIG. 6 is a flow diagram showing a method 508 for performing a recovery process in accordance with embodiments of the invention. The method 508 may include determining recovery conditions (stage 602) with the calculation module 336 based on the elapsed time of treatment and the elapsed time of interruption. The recovery conditions may include a power level to the cooling plate 210 (FIG. 2), a recovery duration, an expected average rate of change of the interface temperature, and/or other suitable parameters.

Another stage 604 of the method 508 may include performing recovery via, e.g., cooling the adipose tissue according to the determined recovery conditions by, for example, activating the power supply 110 (FIG. 1) with the determined power level. In other examples, performing recovery may also include warming or a combination of cooling and warming the adipose tissue. In further examples, performing recovery may also include applying vibration, electrical stimulation, and/or other suitable procedures to the adipose tissue.

A further stage 606 of the method 508 may include monitoring the recovery process. For example, in one embodiment, monitoring the recovery process may include sensing the interface temperature with at least one of the temperature measurement components 217 and 227, converting the sensed interface temperature with the sensing module 330, and calculating a rate of change for the interface temperature with the calculation module 336. In other embodiments, monitoring the recovery process may include monitoring other suitable parameters.

The analysis module 332 may then determine whether the recovery process is satisfactory based on the calculated rate of change of the interface temperature and/or other suitable parameters at stage 608. If the recovery process is not satisfactory, another stage 610 of the method 508 includes adjusting the recovery process with the control module 334, and the process reverts to cooling the adipose tissue at stage 604. If the recovery process is satisfactory, another determination is performed at stage 612 to decide whether the process should return. In one embodiment, the determined recovery conditions include a recovery time, and if the recovery time has not expired, the process reverts to cooling the adipose tissue; otherwise, the process returns. In other embodiments, the operator and/or the subject 101 may terminate the recovery process.

Unless the context clearly requires otherwise, throughout the description and the claims, the words "comprise," "comprising," and the like are to be construed in an inclusive sense as opposed to an exclusive or exhaustive sense, that is to say, in a sense of "including, but not limited to." Words using the singular or plural number also include the plural or singular number, respectively. When the claims use the word "or" in reference to a list of two or more items, that word covers all of the following interpretations of the word: any of the items in the list, all of the items in the list, and any combination of the items in the list.

The various embodiments described above may be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entireties. Aspects of the invention may be modified, if necessary, to employ treatment devices and actuators with a plurality of treatment units, thermally conductive devices with various configurations, and concepts of the various patents, applications, and publications to provide yet further embodiments of the invention.

These and other changes may be made to the invention in light of the above-detailed description. In general, in the following claims, the terms used should not be construed to limit the invention to the specific embodiments disclosed in the specification and the claims, but should be construed to include all cooling that operates in accordance with the claims. Accordingly, the invention is not limited by the disclosure, but instead its scope is to be determined entirely by the following claims.

I claim:

1. A method for treating a subcutaneous lipid-rich region of a subject having skin, comprising:
   heating or cooling the subcutaneous lipid-rich region of the subject according to a profile of a treatment process, the profile having a total duration;
   identifying an interruption in the treatment process after a first duration,
   determining a second duration of the identified interruption;
   determining a third duration equal to a difference between the total duration and the first duration;
   compensating for (1) rewarming of the subcutaneous lipid-rich region of the subject during the second duration when the subcutaneous lipid-rich region is cooled during the first duration and (2) a temperature decrease in the subcutaneous lipid-rich region when the subcutaneous lipid-rich region is heated during the first duration; and
   after compensating for rewarming of the subcutaneous lipid-rich region or the temperature decrease in the subcutaneous lipid-rich region, continuing the treatment process according to the profile for the third duration.

2. The method of claim 1, further comprising determining an interruption temperature ($T_{interrupt}$) of the subcutaneous lipid-rich region after the first duration and a rewarming temperature ($T_{rewarm}$) of the subcutaneous lipid-rich region after the second duration based on the first and second durations, respectively.

3. The method of claim 1, further comprising determining an interruption temperature ($T_{interrupt}$) of the subcutaneous lipid-rich region after the first duration and a rewarming temperature ($T_{rewarm}$) of the subcutaneous lipid-rich region after the second duration based on the first and second durations, respectively, wherein the profile is a first profile, and wherein the method further includes determining a second profile having a cooling rate ($\dot{Q}$) calculated as follows:

$$\dot{Q} = \frac{\rho V C_p (T_{rewarm} - T_{interrupt})}{\pi}$$

where ρ is a density, V is a volume, and $C_p$ is a specific heat capacity of the subcutaneous lipid-rich region; and π is a recovery duration.

4. The method of claim 1, further comprising determining an interruption temperature ($T_{interrupt}$) of the subcutaneous lipid-rich region after the first duration and a rewarming temperature ($T_{rewarm}$) of the subcutaneous lipid-rich region after the second duration based on the first and second durations, respectively, wherein the profile is a first profile, and wherein the method further includes determining a second profile having an expected rate of change for a temperature at the skin of the subject as follows:

$$\Delta T = \frac{(T_{rewarm} - T_{interrupt})}{\pi}$$

where π is a recovery duration.

5. The method of claim 4 wherein compensating for rewarming includes
   monitoring a rate of change for the temperature at the skin of the subject; and
   adjusting the second profile for the recovery process if the monitored rate of change deviates from the expected rate of change by a preselected amount.

6. The method of claim 4 wherein compensating for rewarming includes
   monitoring a rate of change for the temperature at the skin of the subject; and
   adjusting the second profile for the recovery process if the monitored rate of change deviates from the expected rate of change by a preselected percentage.

7. The method of claim 1, further comprising:
   determining a compensation cooling/heating rate based on the second duration; and
   cooling or heating the subcutaneous lipid-rich region based on the compensation cooling/heating rate to compensate for the rewarming or the temperature decrease of the subcutaneous lipid-rich cells.

8. The method of claim 1, further comprising:
   determining whether to resume the treatment process after the identified interruption based on the second duration and/or a number of interruption occurrences;
   if the determination is to resume the treatment process, the treatment process is continued according to the profile for the third duration; and
   if the determination is to not resume the treatment process, the treatment process according to the profile is stopped.

9. A computer-readable medium containing instructions for performing the method of claim 1.

10. A method for treating a subcutaneous lipid-rich region of a subject having skin, comprising:
    heating or cooling the subcutaneous lipid-rich region of the subject according to a profile of a treatment process, the profile having a total duration;
    identifying an interruption in the treatment process after a first duration,
    determining an interrupt duration of the interruption;
    determining a compensation treatment profile based on the interrupt duration, the compensation treatment profile being different from the profile of the treatment process;
    heating or cooling the subcutaneous lipid-rich region according to the compensation treatment profile to compensate for changes in temperature of the subcutaneous lipid-rich region associated with the identified interruption;
    determining a third duration based on the total duration and the first duration; and
    after compensating for the identified interruption, continuing the treatment process according to the profile based on the third duration.

11. The method of claim 10, further comprising:
    determine whether to resume the treatment process based on the interrupt duration and/or a number of interruption occurrences;
    if the determination is to resume the treatment process, the treatment process is continued according to the profile for the third duration; and
    if the determination is to not resume the treatment process, the treatment process is terminated.

12. The method of claim 10, wherein the third duration is equal to a difference between the total duration and the first duration.

13. The method of claim 10, further comprising:
    determining a recovery cooling/heating rate based on the interrupt duration; and cooling or heating the subcutaneous lipid-rich region based on the recovery cooling/heating rate to compensate for the temperature changes of the subcutaneous lipid-rich region associated with the identified interruption.

* * * * *